US012569404B2

(12) United States Patent
Pebley et al.

(10) Patent No.: US 12,569,404 B2
(45) Date of Patent: Mar. 10, 2026

(54) METHODS, SYSTEMS, AND MATERIALS FOR MAKING UNIT DOSAGE FORMS

(71) Applicant: OFD BioPharma, LLC, Albany, OR (US)

(72) Inventors: Walter Pebley, Corvallis, OR (US);
Donald Gray Johnson, Jr., Salem, OR (US); Janardan M. Desai, Brampton (CA); Kevin D. Morgus, Albany, OR (US); Gonzalo Leon Rodriguez, Salem, OR (US); Daniel Joseph Freeman, Albany, OR (US); Daniel Scot Franklin, Albany, OR (US); Kristen N. Roegner, Corvallis, OR (US); Joshua Harvey, Turner, OR (US); Andrew Love, Monmouth, OR (US)

(73) Assignee: OFD BioPharma, LLC, Albany, OR (US)

( * ) Notice: Subject to any disclaimer, the term of this patent is extended or adjusted under 35 U.S.C. 154(b) by 447 days.

(21) Appl. No.: 18/158,845

(22) Filed: Jan. 24, 2023

(65) Prior Publication Data

US 2023/0285245 A1     Sep. 14, 2023

Related U.S. Application Data

(60) Provisional application No. 63/267,091, filed on Jan. 24, 2022.

(51) Int. Cl.
A61J 3/10 (2006.01)
A61K 9/20 (2006.01)

(52) U.S. Cl.
CPC .............. A61J 3/10 (2013.01); A61K 9/2095 (2013.01)

(58) Field of Classification Search
CPC ....... A61K 9/2095; A61K 9/1688; A61J 3/10; B29C 41/26; B29C 31/06
See application file for complete search history.

(56) References Cited

U.S. PATENT DOCUMENTS

| | | | |
|---|---|---|---|
| 5,814,338 A | 9/1998 | Veronesi | |
| 8,158,152 B2 | 4/2012 | Palepu | |
| 9,651,305 B2 | 5/2017 | Gasteyer et al. | |
| 10,539,367 B2 | 1/2020 | Corbin, III et al. | |
| 10,882,654 B2 | 1/2021 | Root et al. | |
| 10,969,171 B2 | 4/2021 | Corbin, III et al. | |
| 2003/0085487 A1 | 5/2003 | Tanner et al. | |
| 2018/0169008 A1 | 6/2018 | Dixit et al. | |
| 2020/0109896 A1 | 4/2020 | Plitzko et al. | |
| 2020/0116428 A1 | 4/2020 | Gebhard et al. | |
| 2020/0237840 A1 | 7/2020 | Morrow | |

OTHER PUBLICATIONS

U.S. Patent and Trademark Office, International Search Report and Written Opinion of the International Searching Authority in PCT/US2023/061170, mailed Jun. 27, 2023, 15 pages.

*Primary Examiner* — Monica A Huson
(74) *Attorney, Agent, or Firm* — Goodwin Procter LLP

(57) ABSTRACT

Systems, methods, and materials are described for making solid unit dosage forms for administration of therapeutic and biotherapeutic agents, particularly dosage forms for various enteral, nasal, pulmonary, vaginal, topical, and other suitable non-injection delivery routes. Contact freezing methods may be used in conjunction with lyophilization or vacuum drying to process a liquid formulation and produce solid unit dosage forms having a high degree of structural stability while preserving the therapeutic activity of the included agents.

21 Claims, 13 Drawing Sheets

_Fig. 1_

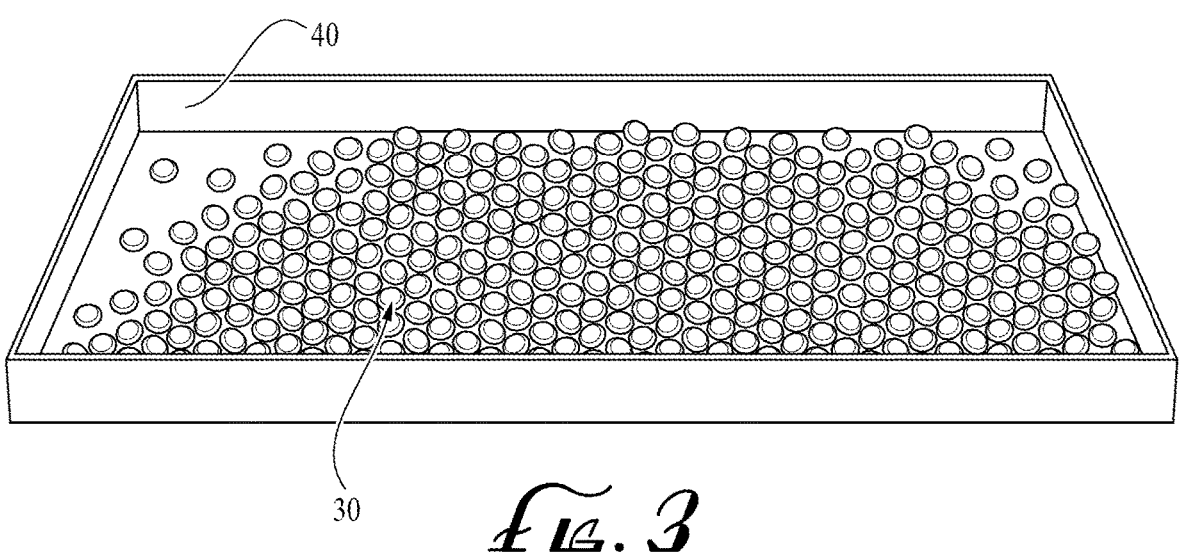
110
20
102
104
106
_fig. 2_
40
30
_fig. 3_

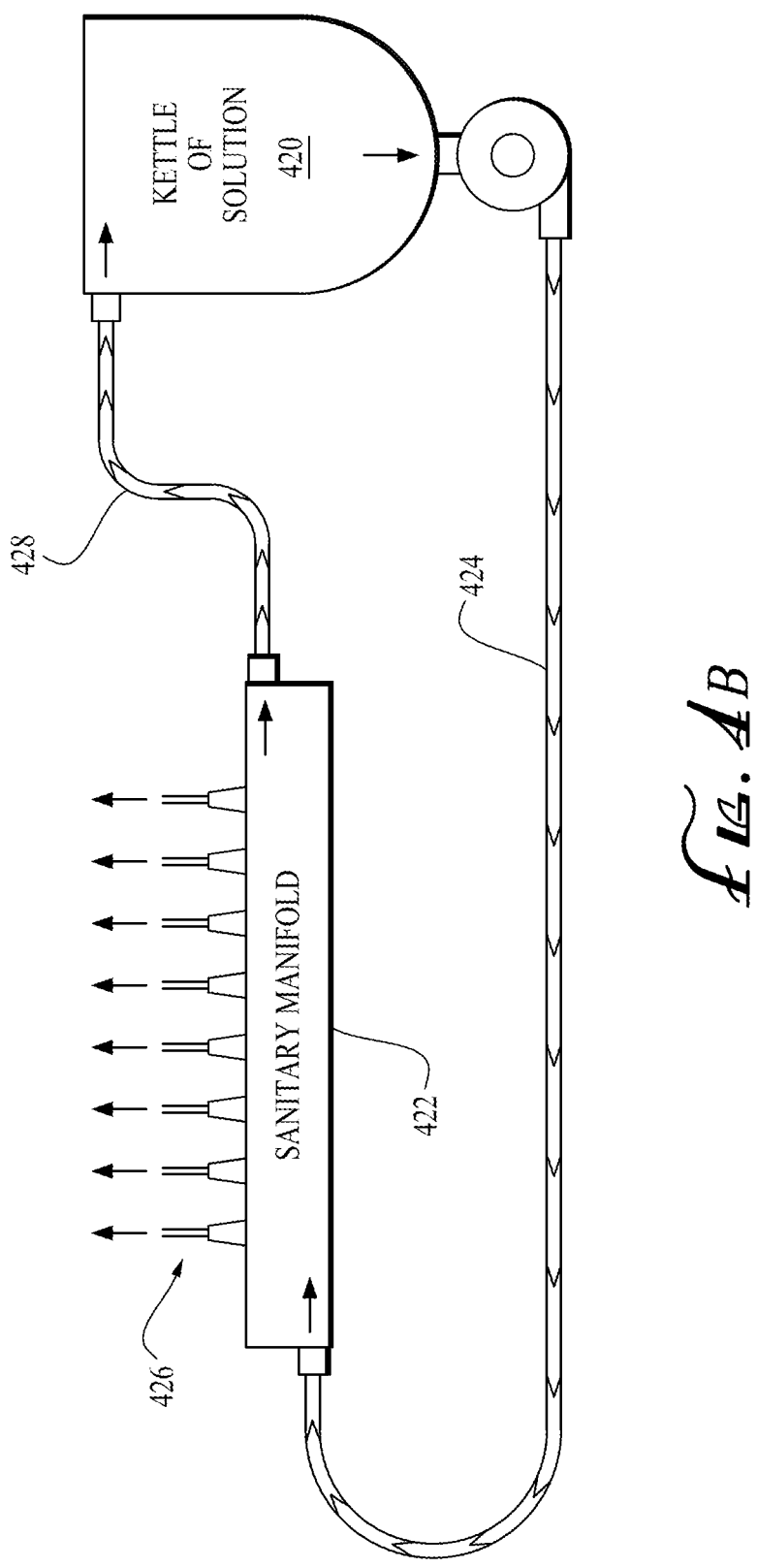
_Fig. 4B_

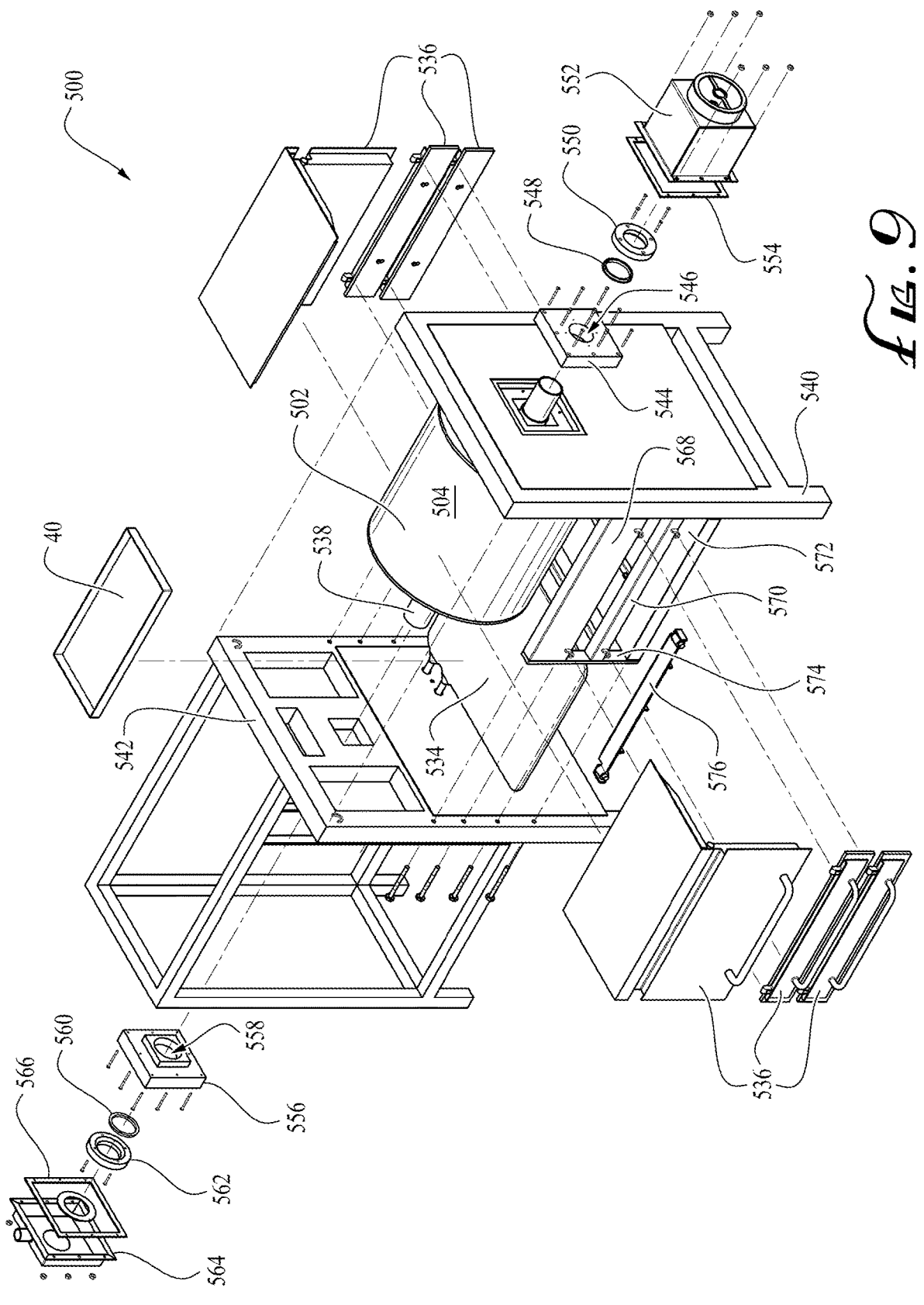
_Fig. 9_

1400

| ROTATING A DRUM AT A DESIRED SPEED | 1402 |
| CHILLING AN OUTER SURFACE OF THE DRUM | 1404 |
| DISPENSING A LIQUID FORMULATION ONTO THE OUTER SURFACE | 1406 |
| FREEZING THE LIQUID FORMULATION AS THE DRUM ROTATES | 1408 |
| COLLECTING FROZEN UNITS FROM THE OUTER SURFACE OF THE DRUM | 1410 |
| DRYING THE FROZEN UNITS TO YIELD SOLID DOSAGE FORMS | 1412 |

METHODS, SYSTEMS, AND MATERIALS FOR MAKING UNIT DOSAGE FORMS

RELATED APPLICATION DATA

This application is a nonprovisional of and claims the benefit under 35 U.S.C. § 119 (e) of U.S. Provisional Patent Application No. 63/267,091, filed Jan. 24, 2022, the disclosure of which is incorporated by reference herein in its entirety.

TECHNICAL FIELD

The present disclosure generally relates to processes and materials for making solid pharmaceutical dosage forms.

BACKGROUND

Conventional processes for preparing lyophilized oral and vial dosage forms typically involve a unit dose manufacturing and packaging approach where the dosage forms are divided into dosage units, each of which is individually sealed in a compartmentalized pack, such as a blister pack or a glass vial. Such processes tend to be cumbersome and may require large and expensive blister forming equipment, blister tray loading, equipment for filling individual cells or vials, freezing and lyophilization/freeze-drying, blister sealing, perforation, cutting into blister packs, placing stoppers on vials, labeling and inspecting vials, and other related methodologies. The footprint and cost of this equipment, coupled with inefficiencies from processing individual blister packs and vials, provides higher cost to manufacture when compared to bulk dosage and packaging of oral delivery vehicles, specifically for buccal or sublingual uptake.

Accordingly, the present inventors have identified a need for an improved and streamlined system and process designed for creating bulk dosage forms while retaining a desired efficacy of the end product. The present inventors have also identified a need for such a system that is adaptable for efficiently producing dosage forms in an array of shapes, sizes, and dosage amounts as desired.

SUMMARY OF THE DISCLOSURE

The present disclosure relates to systems and methods for producing solid pharmaceutical dosage units in bulk. In some embodiments, the system for bulk manufacture of unit dosage forms may include a horizontally mounted drum configured for rotation about its longitudinal axis, the drum having an outer surface with a plurality of cavities shaped to receive and contain a volume of liquid introduced via a dispenser situated for dispensing the liquid into the cavities. The system further includes a cryogenic component operable for chilling the outer surface of the drum to a suitable temperature capable of rapidly freezing the liquid in the cavities to form a frozen unit. The frozen units may thereafter be deposited into a collection tray positioned relative to the drum to receive the frozen units from the cavities as the drum rotates. A dryer may be provided for drying the collected frozen units to yield solid unit dosage forms having a low water activity level for packaging, shelving, and use.

An aspect of the present disclosure is that the drum has an outer surface that is specialized to arrange a liquid formulation deposited thereon into discrete portions comprising precise amounts. In some embodiments, the outer surface comprises a plurality of cavities adapted to control or restrict the flow of deposited liquid, so that the liquid occupies a particular space while it is in contact with the surface. As the liquid solidifies, the resulting solid takes on a shape that is determined at least in part by the shape of the cavity. In some embodiments, the plurality of cavities comprises a series of endless grooves encircling the drum. In other embodiments, the plurality of cavities may comprise a number of discrete pockets arranged on the outer surface of the drum. The pockets may be distributed along the longitudinal axis of the drum, around the circumference of the drum, or both. Each pocket serves as a boundary for a portion of liquid formulation dispensed into said pocket, constraining the liquid during freezing and thereby imparting a particular shape to the resulting solid unit. Similarly, the volume of each pocket determines the range of volumes of solids that may be created and their corresponding potency.

In some embodiments, the system includes one or more interchangeable sleeves into which the cavities are incorporated, where the sleeves are designed to be fitted over the drum and removably secured thereto. In this fashion, the sleeves may provide a series of cavities of differing geometries (e.g., different shapes and sizes) and/or volumes to produce a variety of dosage units with desired dimensions within a single system.

In some embodiments, the system may comprise a specialized rotary drum freezer that is equipped to receive discrete portions of a liquid formulation comprising a therapeutic agent, and freeze said portions to produce frozen units containing precise amounts of the therapeutic agent. As used herein, the term "drum" is intended to be read broadly and may encompass suitable devices having a generally cylindrical configuration as well as other types of configurations such as those having multiple sides. While the methods and systems described herein exemplify employing a drum, other analogous structures used in continuous processes that may be adapted for the uses described herein include belts, platens, and rollers. The drum may comprise an outer surface formed of stainless steel or other material having a high thermal conductivity. In some embodiments, at least part of the outer surface exhibits low wettability, e.g., from highly hydrophobic to superhydrophobic. The interior of the drum may be hollow or circuited so as to allow a cryogen to be introduced into the interior of the drum and to come into thermal contact with the outer surface. The drum is rotatably mounted on an axle or frame so that the drum is rotatable along its longitudinal axis in at least one direction.

As noted above, the system further includes a cryogenic component for chilling the cavities and the outers surface of the drum to a desired temperature, particularly a temperature suited for freezing the portions of liquid formulation deposited in the cavities. In some embodiments, the cryogenic component is designed to establish thermal contact between a cryogen and the outer surface. For example, the cryogenic component may deliver a cryogen to the interior of the drum such that the cryogen comes into thermal contact with the material of the outer surface via contact with interior surfaces of the drum. In some cases, the thermal contact may be indirect, such as through an intervening heat transfer fluid.

The system may further comprise a mechanism for rotating the drum during dispensing of liquid formulation. In various embodiments, said mechanism includes a motor for rotating the drum through operable connection to an axle extending through the longitudinal axis of the drum. The motor may be any suitable motor, such as a variable speed motor, and the mechanism may further include a controller for setting and/or adjusting the speed of rotation as desired.

In some embodiments, a method for bulk manufacture of unit dosage forms may comprise depositing a liquid formulation comprising a therapeutic agent on an outer surface of a rotatable drum or, more particularly, into defined cavities featured in the outer surface of the drum. The outer surface is chilled to an extremely low temperature, such as by exposing the interior of the drum to a cryogenic medium, thereby providing for rapid freezing of the dispensed liquid contained within the cavities of the outer surface of the drum. The method may further comprise rotating the drum so that the deposited liquid formulation is carried through at least a portion of the rotation of the drum while in contact with its outer surface to facilitate freezing of the dispensed portions into frozen units. The method may further comprise collecting each frozen unit or a plurality thereof and drying each unit to yield a unit dosage form having a low water activity level.

As further described in detail herein, use of rapid freezing processes is important to biologic stabilization for lyophilization/freeze-drying. The controlled volumetric delivery associated with the systems and methods described herein provide rapid freezing of a controlled biological efficacious dose (e.g., probiotic stabilization) to maintain both physical shape/volume of the manufactured dosage form and its biological efficacy. Certain therapeutic approaches that may benefit from these disclosed processes include microbial therapeutics, immunotherapy, and cell and gene therapy. Additional aspects and advantages of these and other embodiments will be apparent from the following detailed description of example embodiments, which proceeds with reference to the accompanying drawings.

BRIEF DESCRIPTION OF THE DRAWINGS

The written disclosure herein describes illustrative embodiments that are not intended to be limiting or exhaustive in nature. Reference is made to certain of such illustrative embodiments that are depicted in the figures, in which:

FIG. 1 is an enlarged view of a subset of elements of a freezer system in accordance with one embodiment.

FIG. 2 is an enlarged view of the freezer system of FIG. 1 with components removed to illustrate additional details of a nozzle in accordance with one embodiment.

FIG. 3 illustrates a batch of frozen dosage units produced via the freezer system of FIG. 1 in accordance with one embodiment.

FIG. 4B illustrates a process flow featuring additional elements of a freezer system in accordance with one embodiment.

FIG. 9 is an exploded view of the freezer system of FIG. 5, with a dispenser removed to avoid obscuring more pertinent aspects of the freezer system.

DETAILED DESCRIPTION OF EXAMPLE EMBODIMENTS

Figure 4A:
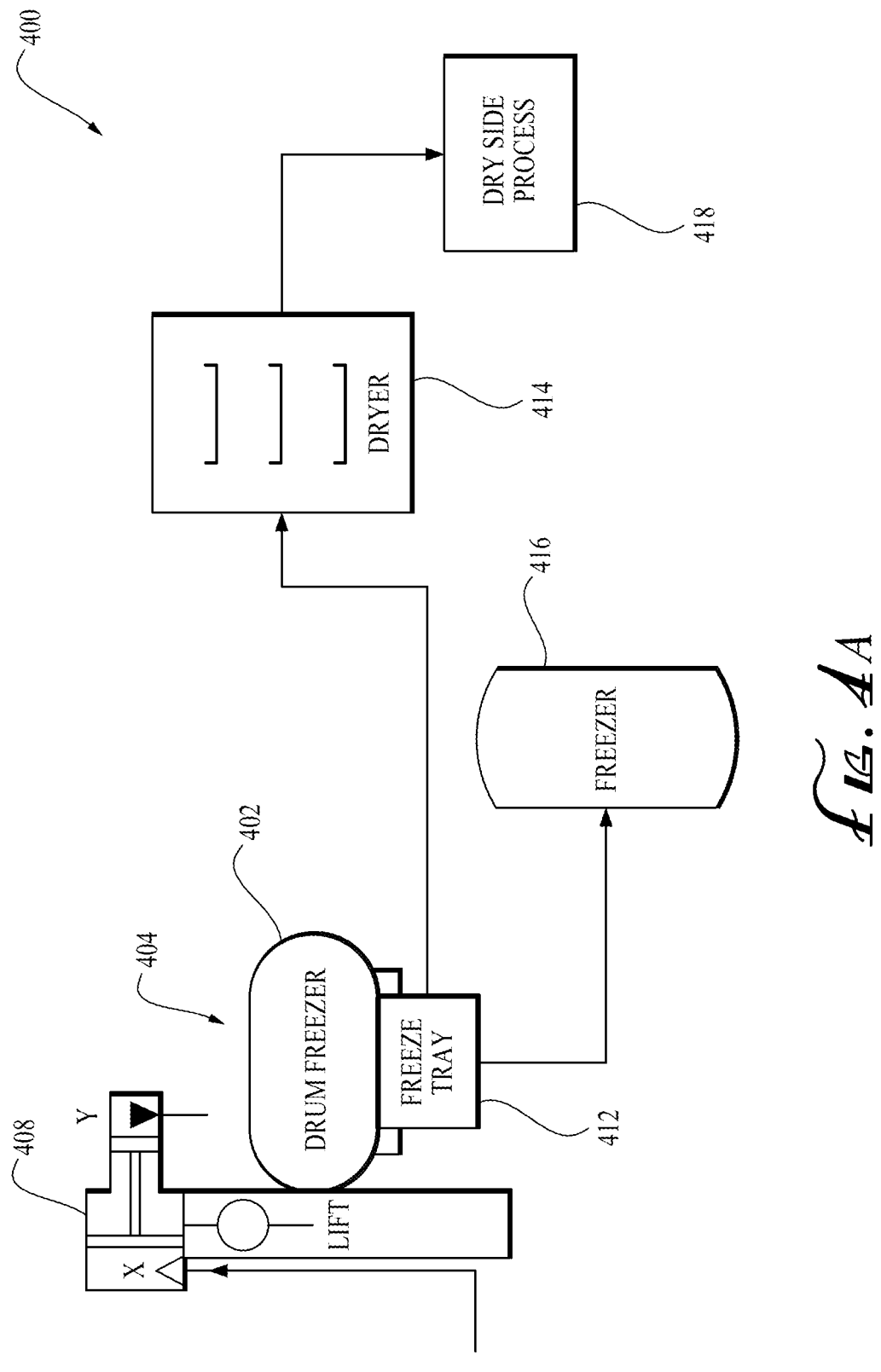
FIG. 4A illustrates a process flow featuring elements of a freezer system in accordance with one embodiment.

With reference to the drawings, this section describes various embodiments of a freezer system and its detailed construction and operation. Throughout the specification, reference to "one embodiment," "an embodiment," or "some embodiments" means that a described feature, structure, or characteristic may be included in at least one embodiment of the freezer system. Thus, appearances of the phrases "in one embodiment," "in an embodiment," or "in some embodiments" in various places throughout this specification are not necessarily all referring to the same embodiment. Furthermore, the described features, structures, and characteristics may be combined in any suitable manner in one or more embodiments. In view of the disclosure herein, those skilled in the art will recognize that the various embodiments illustrated and described herein can be practiced without one or more of the specific details or with other methods, components, materials, or the like.

The present disclosure sets forth embodiments of a freezer system and related methods for making solid unit dosage forms for administration of therapeutic and biotherapeutic agents, particularly dosage forms for enteral, sublingual, buccal, nasal, pulmonary, vaginal, topical, or other suitable non-injection delivery routes. One objective of the disclosed systems and methods is to manufacture solid unit dosage forms as an alternative to injections where oral, inhalation, or pulmonary delivery of precise potency is required, thereby facilitating the development of treatment conditions not requiring a cold chain and/or specialized professionals for applying treatments.

Briefly, the freezer systems further described in detail below include a rotatable drum having an exterior surface with a plurality of cavities formed thereon, where the cavities receive a volume of liquid containing the therapeutic agents from a dispenser. The system further includes a cryogenic component operable for chilling the outer surface of the drum to freeze the liquid in the cavities and form a frozen unit. In some embodiments, a dryer may be used to dry the frozen units to yield solid unit dosage forms having a low water activity level for packaging and use.

The present disclosure describes using high-throughput production processes for making solid unit dosage forms in bulk that can be readily packaged either in bulk or in individual dose formats for storage, transportation, and further processing. As described herein, contact freezing methods can be used in conjunction with lyophilization or vacuum drying to process a liquid formulation and produce solid unit dosage forms having a high degree of structural stability while preserving the therapeutic activity and efficacy of the included agent(s).

As further described in detail below, the disclosed embodiments provide several advantages and benefits as compared to conventional methodologies. For example, the disclosed systems and methods provide for a larger production volume in a lyophilization chamber (batch) and a higher throughput rate as compared to a blister format. Moreover, the disclosed systems accommodate formulation-specific controlled freezing rates for maximum biological retention and efficacy of the dosage unit. In addition, the disclosed systems and methods are streamlined to yield a lower total production cost per dose as compared to a blister process and much less packaging per dose over the manufacturing process. Finally, the disclosed systems and methods allow for smaller dose delivery by routes that avoid the first pass effect, a phenomenon where the concentration of a drug is reduced before it reaches a site of action or the systemic circulation.

With collective reference to FIGS. 1-4, the following discussion proceeds with a general overview of an example freezer system and related methods for making solid unit dosage forms containing one or more therapeutic agents, followed by a more detailed discussion of another example embodiment of a freezer system with particular reference to FIGS. 5-13. Additional details of these and other embodiments of a freezer system are further discussed below with reference to the accompanying figures.

FIGS. 1-2 are each enlarged views of a portion of a freezer system 100 in accordance with one embodiment. With general reference to FIGS. 1-2, the freezer system 100 includes a drum 102 mounted horizontally to a frame (see frame 530 in FIG. 5) for rotation about a longitudinal axis. The drum 102 has an outer surface 104 with a plurality of cavities 106 formed thereon. In some embodiments, the cavities 106 may comprise a series of parallel channels or grooves encircling the drum 102 (as shown in FIGS. 1 and 2). In other embodiments, the plurality of cavities 106 may instead comprise a number of discrete pockets (not shown) arranged on the outer surface 104 of the drum 102. The pockets may be distributed along the longitudinal axis of the drum 102, around the circumference of the drum 102, or both. In still other embodiments, the cavities 106 may include any suitable shape or size to impart a particular configuration to the resulting solid unit as further described below.

The freezer system 100 further includes a dispenser 108 operable for dispensing liquid formulation containing one or more therapeutic agents. In some embodiments, the liquid formulation has a temperature of about 4° C. to about 25° C. during dispensing. The dispenser 108 may include an array of nozzles 110 or other suitable mechanisms arranged for dispensing the liquid formulation onto the outer surface 104 of the drum 102, and particularly into the cavities 106. The dispenser 108 dispenses the liquid formulation as the drum 102 rotates such that the liquid is contained within the cavities 106 and assumes a shape and volume based at least in part upon the dimensions of the cavities 106.

In some embodiments, the dispenser 108 comprises a plurality of nozzles 110 arranged in parallel along the longitudinal axis of the drum 102 so that each nozzle 110 is directed to a distinct zone of the outer surface 104 of the drum 102. As noted above, a plurality of cavities 106 may also be distributed along the longitudinal axis of the drum 102 as well as around its circumference. Accordingly, in some embodiments, each nozzle 110 may be aligned with at least one cavity 106. For example, where the cavities 106 comprise grooves (as shown in FIG. 1), each nozzle 110 may be aligned with a respective groove 106 for dispensing liquid formulation into the groove 106 as the drum 102 rotates. In another example, where the cavities 106 instead comprise pockets (not shown), each nozzle 110 may come into radial alignment with at least one corresponding pocket 106 at some point in a full rotation of the drum 102 for dispensing liquid formulation into the pocket as the drum 102 rotates. In some embodiments, multiple pockets 106 may be arranged around the circumference of the drum 102 at a given point along its rotational axis, such that a single nozzle 110 may dispense liquid formulation into some or all of said pockets 106 during a rotation of the drum 102.

The freezer system 100 further includes a cryogenic component (not shown) operable for chilling the outer surface 104 of the drum 102 to a suitable temperature for freezing the liquid in the cavities 106 to form a frozen dosage unit as further discussed below with reference to FIGS. 2-4. In some embodiments, the cryogenic component may establish thermal contact between a cryogen and the outer surface 104 of the drum 102. For example, the cryogenic component may deliver a cryogen to the interior of the drum 102 such that the cryogen comes into thermal contact with the material of the outer surface 104 via contact with interior surfaces of the drum 102. In other embodiments, the thermal contact may be indirect, such as through an intervening heat transfer fluid.

Cryogens for use in the embodiments described herein may include any material capable of absorbing large amounts of heat to produce very low temperatures in adjacent materials upon changing from one state to another, for example, from a liquid or solid state to a gaseous state. The cryogen may comprise a cryogenic solid, cryogenic gas, cryogenic liquid, or a heat transfer fluid. In some embodiments, the cryogen is a liquid cryogen. Any suitable cryogenic liquid having a very low boiling temperature may be used. Examples include, without limitation, liquid helium, liquid argon, liquid carbon dioxide, liquid oxygen, and liquid nitrogen or supercooled ammonia. The liquid can also be chemically inert. In certain embodiments, the cryogen is liquid nitrogen. In some embodiments, the cryogen is delivered to the drum as a liquid but is brought into thermal contact with the outer surface as a vapor, a liquid/vapor mixture, or as a gas. For example, a liquid cryogen may be injected into the drum and then atomized, such as by a fan, where the resulting vapor is brought into thermal contact with the outer surface. Used cryogen may be recaptured from the drum, condensed as needed, and recycled for further chilling of the outer surface or directed to other uses.

With collective reference to FIGS. 2-4, the following provides additional details of a process for manufacturing frozen dosage units 30 via the freezer system 100. For ease of understanding and to avoid obscuring relevant components of the disclosed embodiment, the freezer system 100 illustrated in FIG. 2 has been modified to remove the dispenser 108 and illustrate a single nozzle 110.

As described with reference to FIG. 1, the freezer system 100 includes a dispenser 108 situated for dispensing liquid formulation via a parallel array of nozzles 110 onto an outer surface 104 of a drum 102. The drum 102 includes a plurality of cavities 106 on its outer surface 104 and a cryogenic component operable for freezing the liquid formulation within the cavities 106 after deposition. With particular reference to FIG. 2, the freezer system 100 may be adapted to provide for controlled dispensing of liquid formulation via the nozzle 110 into the cavities 106. More particularly, the freezer system 100 is adapted for dispensing precise amounts of the liquid formulation with a specific timing relative to a rotation cycle of the drum 102. Stated differently, the dispenser 108 and the rotational mechanism that drives the drum 102 may be cooperatively controlled such that the nozzle 110 dispenses a plurality of discrete, precisely measured portions of liquid formulation into the cavities 106 during each rotation of the drum 102. Further, the temperature of the outer surface 104 of the drum 102 may be selected so that each dispensed portion of liquid formulation achieves a desired level of freezing within a single rotation cycle of the drum 102 after being dispensed. In some embodiments, the freezer system 100 is equipped to provide a target outer surface temperature so that each dispensed portion of liquid formulation is sufficiently frozen and ready for collection prior to the drum 102 completing a rotation cycle. For example, in some embodiments, the liquid formulation may be frozen within a one-half rotation of the drum 102.

As illustrated in FIG. 2, the nozzle 110 dispenses a plurality of discrete dosage portions 20 of the liquid formulation into one of the plurality of grooves 106 on the outer surface 104 of the rotating drum 102. The cryogenic component of the freezer system 100 cools the outer surface 104 to a target temperature so that each dosage portion 20 begins to freeze upon deposition and continues freezing as the drum 102 rotates to form a frozen dosage unit 30 (see FIG. 3). The rotation of the drum 102 allows for sustained deposition of the liquid formulation at a given frequency so that each cavity 106 may contain multiple dosage portions 20 at varying stages of freezing.

Preferably, the outer surface 104 of the drum 102 is configured so that the liquid formulation deposited into a cavity 106 ultimately freezes to form a solid dosage unit 30 with minimal to no adherence to the cavity 106. In some embodiments, at least a part of the outer surface 104, particularly the portion bounded between the cavity 106, is configured to exhibit low wettability with respect to the liquid formulation, where said surface wettability may range from highly hydrophobic to superhydrophobic. In an aspect thereof, the hydrophobicity can be expressed in terms of the contact angle exhibited by a water droplet on said surface, where said surface exhibits a water contact angle of at least 120°, or more particularly at least 150°. In another aspect, the outer surface 104 within the cavity 106 may provide a low sliding angle, e.g., an angle of inclination of the outer surface 104 at which a frozen dosage unit 30 will slide off. In some embodiments, the outer surface 104 within the cavity 106 is configured to provide a sliding angle of about 90° or less, or more particularly 60° or less, or 45° or less.

In some embodiments, the outer surface 104 of the drum 102 may include any suitable surface morphology and/or surface chemistry to minimize adhesion of the frozen dosage unit 30. For example, the outer surface 104 may include morphological features, such as surface roughness, configured at the micro- and/or nano-scale to allow for an air layer to be maintained in the space between asperities during liquid contact. The surface chemistry may be configured to exhibit a lower surface energy and reduce wettability. In some cases, the outer surface 104 may include a coating that increases the hydrophobicity of the outer surface 104.

Once the dosage units 30 have been frozen on the outer surface 104 of the drum 102, the dosage units 30 may be collected as they drop off the drum 102. In the configuration of the freezer system 100 described above with reference to FIGS. 1-2, the liquid formulation may be dispensed via the nozzles 110 into the cavity 106 of the outer surface 104 of the drum 102 near the highest point of its orbital path to maximize contact time with the outer surface 104. Once the dosage unit 30 is frozen, it can be subsequently removed from the outer surface 104 near the lowest point of the orbital path of the drum 102. As mentioned above, the cavity 106 may include a surface configured to facilitate separation of the frozen dosage unit 30 from the cavity 106 by tilting the cavity 106 without need for a physical dislodging mechanism. In such embodiments, the cavity 106 is shaped so that the frozen unit 30 therein will fall out when the cavity 106 is tilted. In other embodiments, the freezer system 100 may include a dislodging mechanism (e.g., a structure of the type commonly referred to as a doctor blade or doctor knife) that enters each cavity 106 at a certain point in the rotation cycle of the drum 102 and dislodges the frozen dosage unit 30 contained therein.

Once the frozen dosage units 30 have been removed from the cavities 106 of the drum 102, the frozen dosage units 30 may be collected in a tray 40 (see FIG. 3) positioned relative to the drum 102 to receive the frozen units. In some embodiments, the collection tray 40 may be chilled to a selected temperature to preserve the frozen dosage units 30 in a frozen state and/or to ensure the frozen dosage units 30 have reached a desired level of freezing. In some embodiments, the collection tray 40 is equipped to collect a quantity of frozen units 30, for example, the total number of frozen units 30 produced during multiple rotation cycles.

As noted previously, the present disclosure encompasses methods and systems for producing solid unit dosage forms 30 having a low water content and/or low water activity level. Accordingly, in some embodiments, the freezer system 100 may further include a dryer (see dryer 414 of FIG. 4) for drying frozen dosage units 30 collected after freezing. The dryer may comprise a freeze dryer, a vacuum dryer, or other apparatus suitable for removing liquid content, e.g., a solvent, from the frozen dosage units 30 while preserving their structural integrity. In certain embodiments, the dryer comprises a freeze dryer, or at least an apparatus adapted to accomplish lyophilization, i.e, sublimation of water and/or other solvent into vapor, under low pressure.

FIGS. 4A and 4B collectively illustrate an example process flow 400 featuring an embodiment of the freezer system 100 described herein. With reference to FIG. 4A, the dispenser 408 containing the liquid formulation with one or more therapeutic agents dispenses the liquid formulation onto a chilled drum 402 at a high point of its rotation cycle to be frozen into frozen units as described with reference to FIGS. 1-3. A collection freeze tray 412 is positioned for collection of the frozen units as they are released from the drum 402 at a low point of its rotation cycle. The batch of frozen units may thereafter be transferred to a freezer 416 for storage or transferred to a freeze dryer 414 for lyophilization and/or other dry side processes 418.

With particular reference to 4B, the freezer system 100 may include a vessel 420 for storing a liquid formulation. In some embodiments, the vessel 420 may be equipped to accomplish or complete preparation of the liquid formulation. The vessel may be operably connected to a manifold 422, wherein the manifold 422 distributes a stream 424 of liquid formulation from the vessel 420 into a plurality of output streams 426 directed to one or more dispensers, such as dispenser 408. Formulation flow in excess of the manifold output may be returned to the vessel 420 as a return stream 428 and recirculated.

With collective reference to FIGS. 5-13, the following provides additional details of a freezer system 500 for making frozen dosage units containing one or more therapeutic agents. The freezer system 500 may include many of the same components and operate in a similar fashion as previously described with reference to the freezer system 100 of FIGS. 1-4. Accordingly, to avoid duplication, some of these components may not be further described in detail in the discussion below with the understanding that similar components described with reference to the freezer system 100 may be incorporated into the freezer system 500.

FIGS. 5-9 collectively illustrate various views of a freezer system 500 in accordance with one example embodiment. With general reference to FIGS. 5-9, the freezer system 500 includes a drum 502 having an outer surface 504 with a plurality of cavities (not shown) formed thereon, the cavities receiving a liquid formulation from a dispenser 508 (such as via nozzles 510) arranged along the longitudinal axis of the drum 502 and directed toward the outer surface 504 of the drum 502 in a similar fashion as described previously with reference to freezer system 100. With reference to the exploded view of FIG. 9 (dispenser 508 removed from view to avoid obscuring more pertinent aspects of the embodiment), the drum 502 is rotatably mounted to a drum frame 530 for rotation relative to the drum frame 530. In one example configuration, the drum 502 includes a drum axle 538 extending along a longitudinal axis through the drum 502, the drum axle 538 mounted to the drum frame 530 along a first support structure 540 and along an opposite second support structure 542. Each of the first and second support structures 540, 542 includes an axle mount 544, 556 coupled thereto, the axle mount 544, 556 having an opening 546, 558 with a diameter corresponding to that of the drum axle 538 such that a portion of the drum axle 538 extends through the respective openings 546, 558 and supported by the axle mount 544, 556. The freezer system 500 further includes a nitrogen seal 548, 560 (made of Teflon or other suitable material), a seal retainer 550, 562, and a shroud 552, 564 and shroud seal 554, 566 (made of silicone or other suitable material) all coupled to the axle mount 544, 556 to enclose the interior of the freezer system 500 and maintain an appropriately sealed environment.

Figure 8:
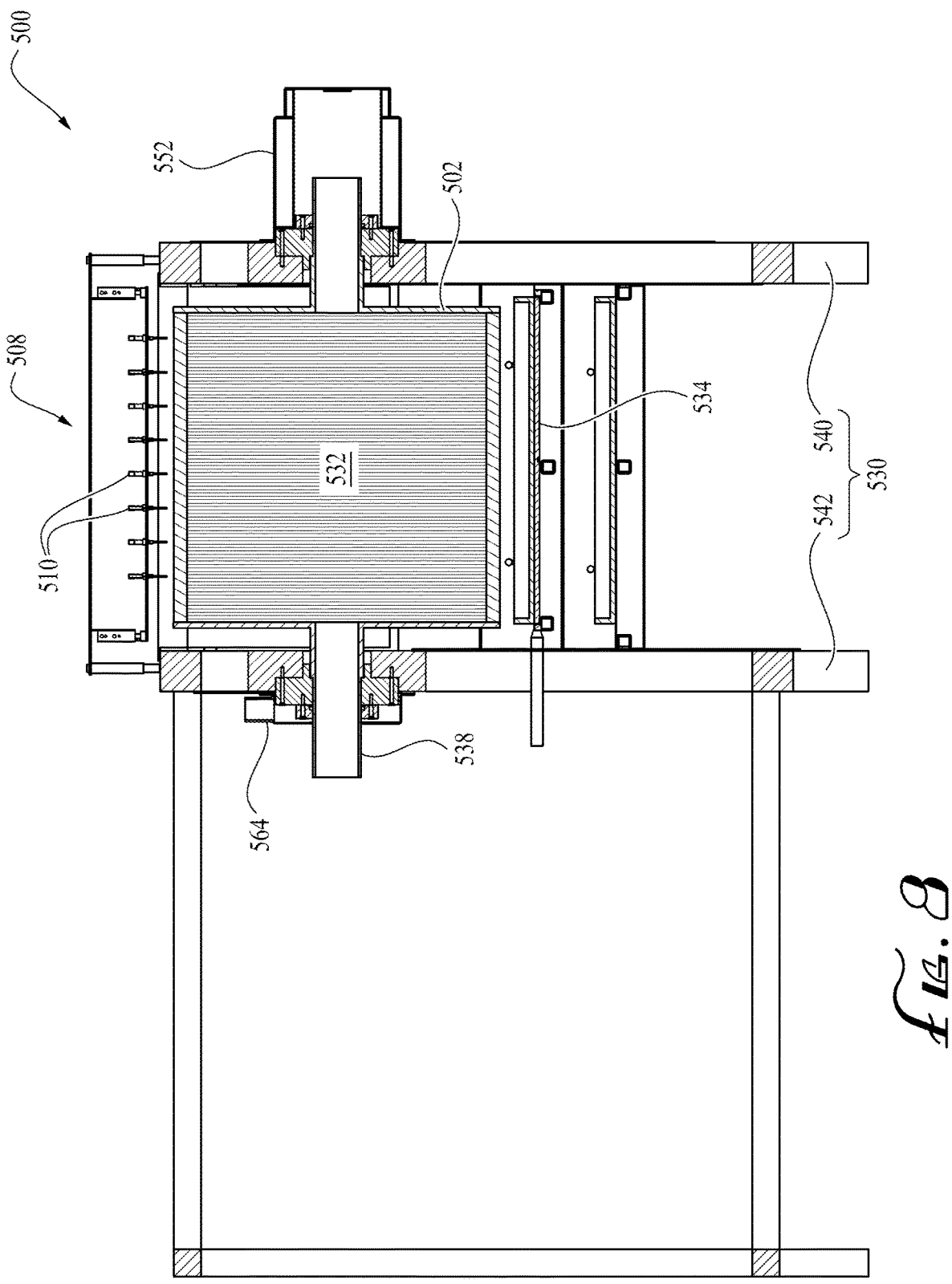
FIG. 8 is a cross-section view of the freezer system of FIG. 5, the cross-section taken at section 8-8 illustrated in FIG. 6.

With particular reference to FIGS. 8 and 9, the drum 502 may include a hollow interior 532 to provide for cooling the outer surface 504 of the drum 502 (e.g., by use of a cryogen) from within as described previously with reference to the freezer system 100 of FIGS. 1-4. Briefly, the cryogen (such as a liquid nitrogen or other suitable component) may be delivered to the hollow interior 532 where it comes into thermal contact with the outer surface 504 to chill the outer surface 504 to a suitable temperature. It should be understood that in other embodiments, other suitable configurations may be arranged to cool the outer surface 504 of the drum 502 to a desired temperature without departing from the principles of the disclosed embodiment.

The outer surface temperature may be selected based upon the properties of the liquid formulation being processed by the freezer system 500 so as to provide a cooling of a dispensed portion of the liquid formulation to a target temperature at a particular rate. In certain embodiments, the cryogenic component of the freezer system 500 is configured such that the temperature of the outer surface 504 is less than about −50° C. In other embodiments, the outer surface temperature may be less than about −80° C., less than about −90° C., less than about −100° C., less than about −110° C., less than about −120° C., less than about −130° C., less than about-140° C., less than about −150° C., up to and including less than −270° C. Stated another way, the outer surface temperature may broadly range from about −50° C. to about −270° C., from −50° C. to about −150° C., from about −60° C. to about −130° C., or from about −80° C. to about −120° C., or from about depending on the liquid formulation and the desired freezing characteristics of the dosage unit. A temperature may be selected that results in supercooling of the portion of liquid formulation so as to produce homogenous nucleation. For example, in liquid formulations comprising living cells, cooling below the $T_g$ (glass transition temperature) of pure water suspends all molecular processes and prevents free radical generation, thereby preserving viability. However, cooling too rapidly can result in the formation of ice crystals that can disrupt cellular structure, while cooling too slowly can result in dehydration and other osmotic damage to the cells. In such cases, the temperature can be selected to provide a rate of cooling from about 0.9° C./min to about 2° C./min.

With particular reference to FIG. 9, the freezer system 500 further includes interior cross bars 568, 570, 572 extending between and mounted to the first and second support structures 540, 542 via a brace 574. In one embodiment, the middle cross bar 570 supports a cooling plate 534 that operates to chill the collection tray 40 arranged underneath the drum 502 to collect the frozen units 30 (see FIG. 3) from the drum 502 and maintain them in a frozen state. In some embodiments, the upper cross bar 568 (or other suitable structure within the first and second support structures 540, 542) supports a scraper bar assembly 576 to dislodge the frozen units 30 from the drum 502 as the drum 502 rotates. The freezer system 500 may further include one or more doors 536 configured to shield the drum 502 and/or the frozen units 30 from the surrounding environment when closed and to provide access to the collection tray 40 when opened to retrieve the frozen units 30.

Figure 5:
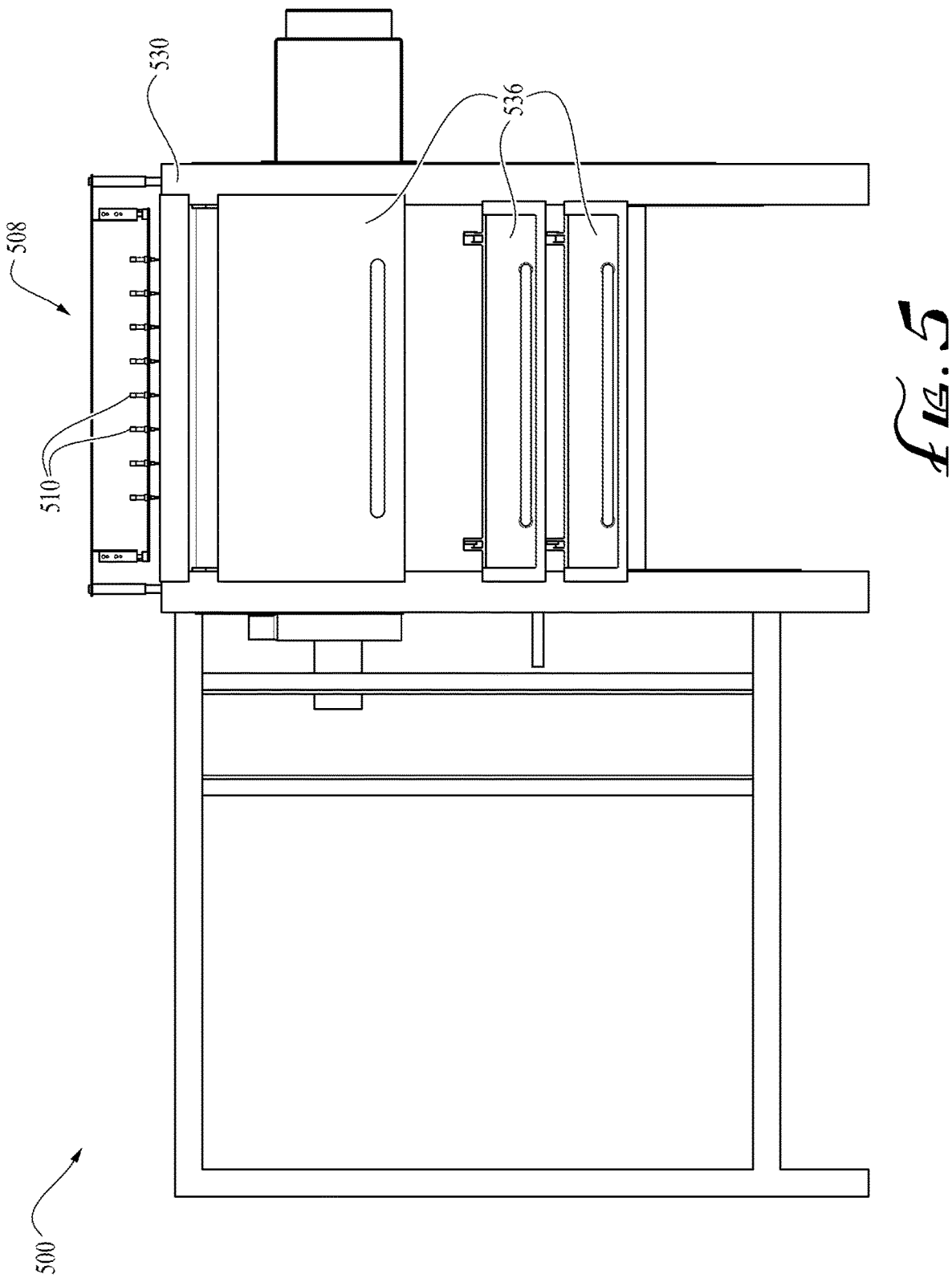
FIG. 5 is a front view of a freezer system in accordance with one embodiment.
Figure 6:
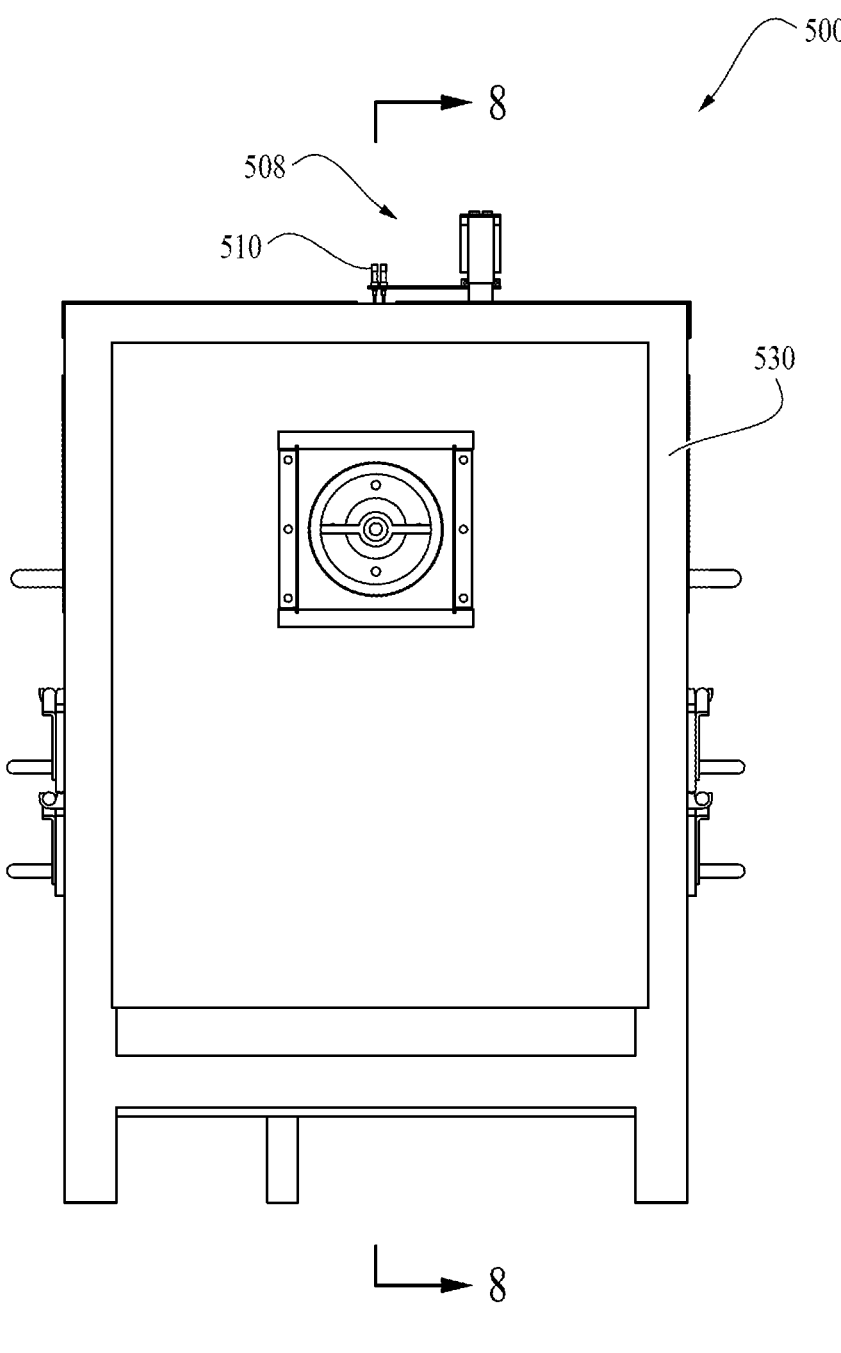
FIG. 6 is a side view of the freezer system of FIG. 5.
Figure 7:
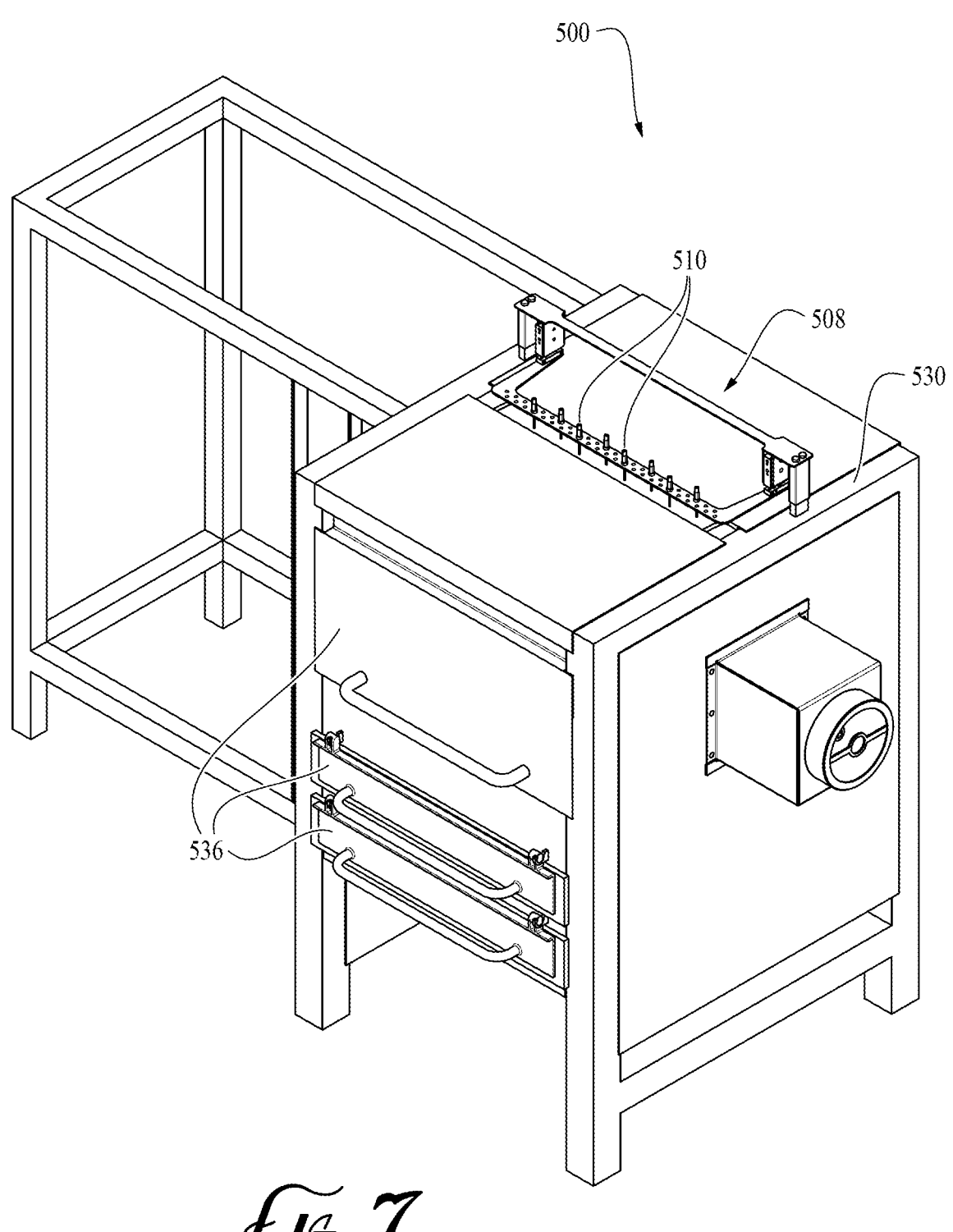
FIG. 7 is a top perspective view of the freezer system of FIG. 5.
Figure 10:
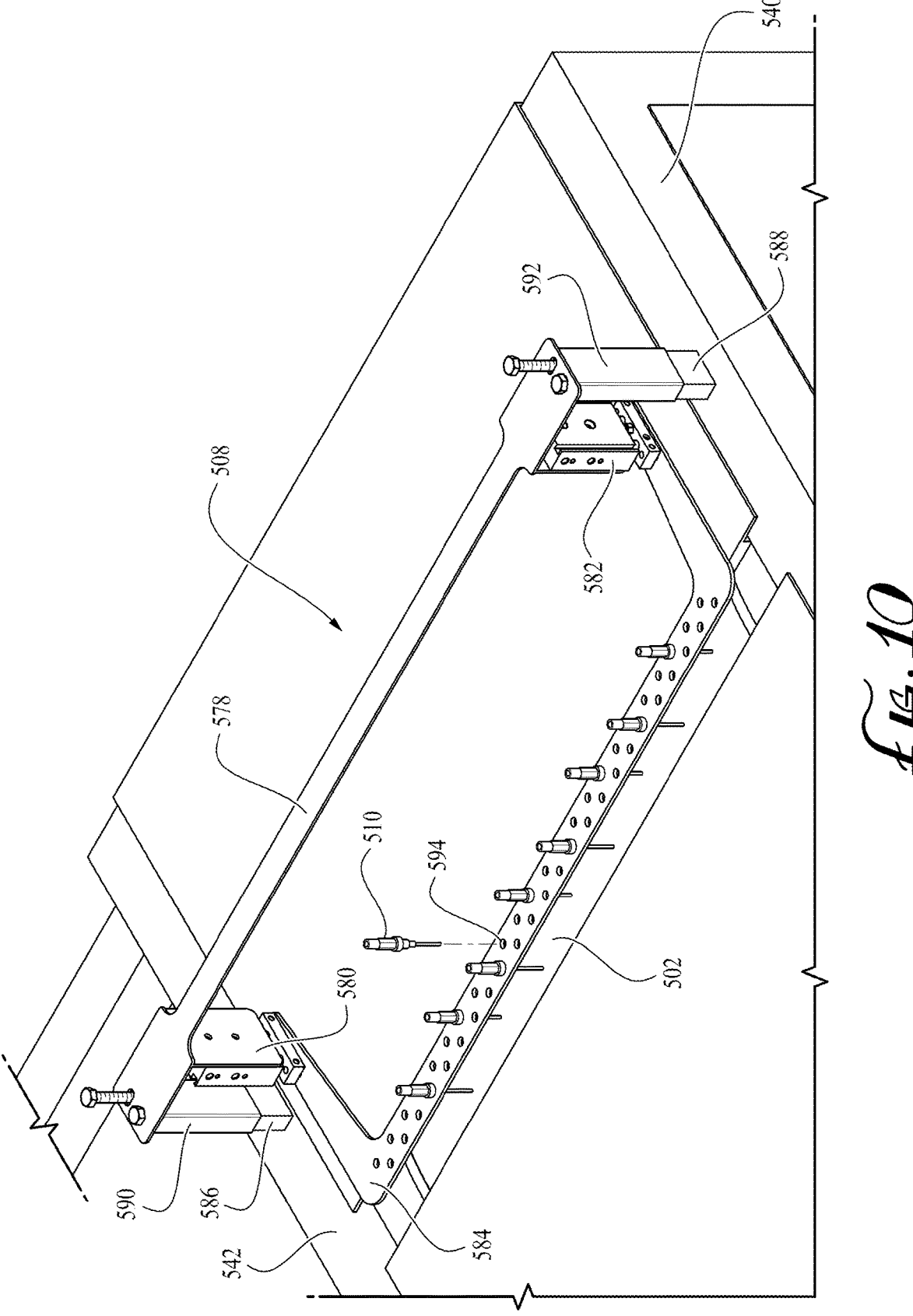
FIG. 10 is an enlarged view illustrating a dispenser of the freezer system of FIG. 5.

FIG. 10 is an enlarged view illustrating additional details of the dispenser 508 of the freezer system 500 of FIG. 5. With reference to FIG. 10, the dispenser 508 includes a cross bar 578 supporting a first guide 580 and a second guide 582, and a nozzle bar 584 with opposing ends thereof coupled to the first and second guides 580, 582. The dispenser 508 further includes a first mount 586 coupled to the first support structure 540 of the drum frame 530 and a second mount 588 coupled to the second support structure 542 of the drum frame 530. The mounts 586, 588 may be coupled to the drum frame 530 in any suitable manner, such as via fastening mechanism or welding. The dispenser 508 further includes a first adjustment sleeve 590 and a second adjustment sleeve 592 coupled to the first and second mounts 586, 588, respectively. The cross bar 578 is coupled along its ends to the adjustment sleeves 590, 592. In this configuration, the adjustment sleeves 586, 588 are adjustable relative to the respective first and second mounts 586, 588 to facilitate a desired height adjustment of the dispenser 508 relative to the drum 502 as needed. As illustrated in FIG. 10, the nozzle bar 584 includes a plurality of staggered openings 594 formed thereon for supporting the nozzles 510 of the dispenser 508 in any suitable configuration relative to the outer surface 504 of the drum 502.

Figure 11:
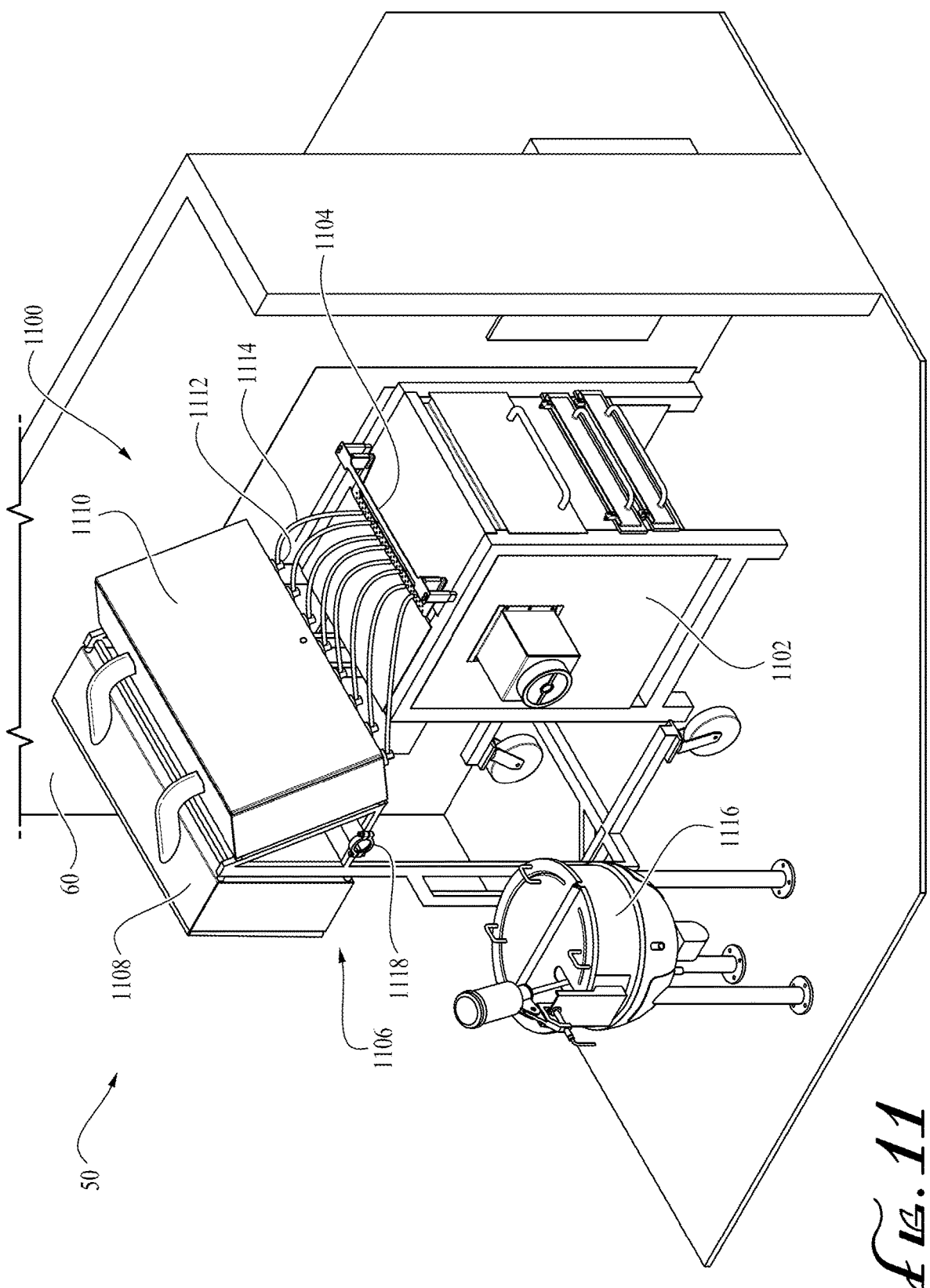
FIG. 11 illustrates an embodiment of a freezer system including a feeding mechanism in accordance with one embodiment.

FIG. 11 illustrates an embodiment of a fully assembled freezer system 1100 in a deployed configuration in accordance with one embodiment. With reference to FIG. 11, the freezer system 1100 includes a drum frame 1102 housing a rotatable drum (not shown) along with the other components described previously with respect to the freezer system 500 of FIGS. 5-10. To establish a frame of reference, the freezer system 1100 illustrated in FIG. 11 is deployed partially in a cleanroom 50, with the drum, dispenser 1104, collection tray (housed within the drum frame 1102), and other components for making the frozen dosage units 30 (see FIG. 3) positioned within the cleanroom 50 to ensure the frozen dosage units 30 are manufactured in a sterile environment. The motor or other suitable drive mechanism (not shown) for the drum is located outside the cleanroom 50 on the other side of the wall 60.

As illustrated in FIG. 11, the system 1100 includes a cabinet frame 1106 including a controller cabinet 1108 for controlling various aspects of the manufacturing process, such as rotation speed of the drum, temperature of the outer surface of the drum, dispensed amount of liquid formulation via the dispenser 1104, and other features of the freezer systems 100, 500, 1100 described herein. The cabinet frame 1106 further includes a pump cabinet 1110 having a series of pumps 1112 connected via conduits 1114 (e.g., hoses or other suitable conduits) to the nozzles (not shown) of the dispenser 1104. The conduits 1114 may all be of equal length to assure the liquid formulation is uniformly distributed to the dispenser 1104. The pump cabinet 1110 is in fluid communication with a kettle 1116 containing the liquid formulation with the one or more therapeutic agents, where the pump cabinet 1110 is operable to draw the liquid formulation from the kettle 1116 for delivery to the nozzles of the dispenser 1104 for distribution onto the outer surface of the drum as described previously. In some embodiments, the liquid formulation from the kettle 1116 may be pumped to a holding tube 1118 that is open to the air to avoid introducing pressure into the process.

As noted above, the freezer systems 100, 500, 1100 described herein may be configured for operation in a controlled environment, such as a cleanroom 50. For example, use of such systems to produce frozen dosage forms 30 of therapeutic agents may involve maintaining a level of air quality to avoid contamination of the product by airborne particles. In some embodiments, at least some components of the system (as described above) may be placed in the cleanroom 50, such as defined under ISO 14644. More particularly, the cleanroom 50 may be compliant with an ISO 14644 standard applicable to the product being made. In some embodiments, the freezer systems 100, 500, 1100 may be configured for operation with or without an operator present in the cleanroom 50.

For example, the system 1100 may include a remote-control device (not shown) in operable communication with the controller cabinet 1108 that is connected to at least the dispenser 1104 and the drum freezer (not shown), so that these components may be situated in the cleanroom 50 while their respective functions, such as dispensing liquid formulation and rotation of the drum, are controllable from outside the cleanroom 50. In some embodiments, additional components and functions of the system 1100 are also controllable by the remote-control device, such as cooling of the drum outer surface and/or collection tray, collection of frozen units, and lyophilization of frozen units. In some embodiments, one or more of the above functions may be automated.

Figures 12, 13:
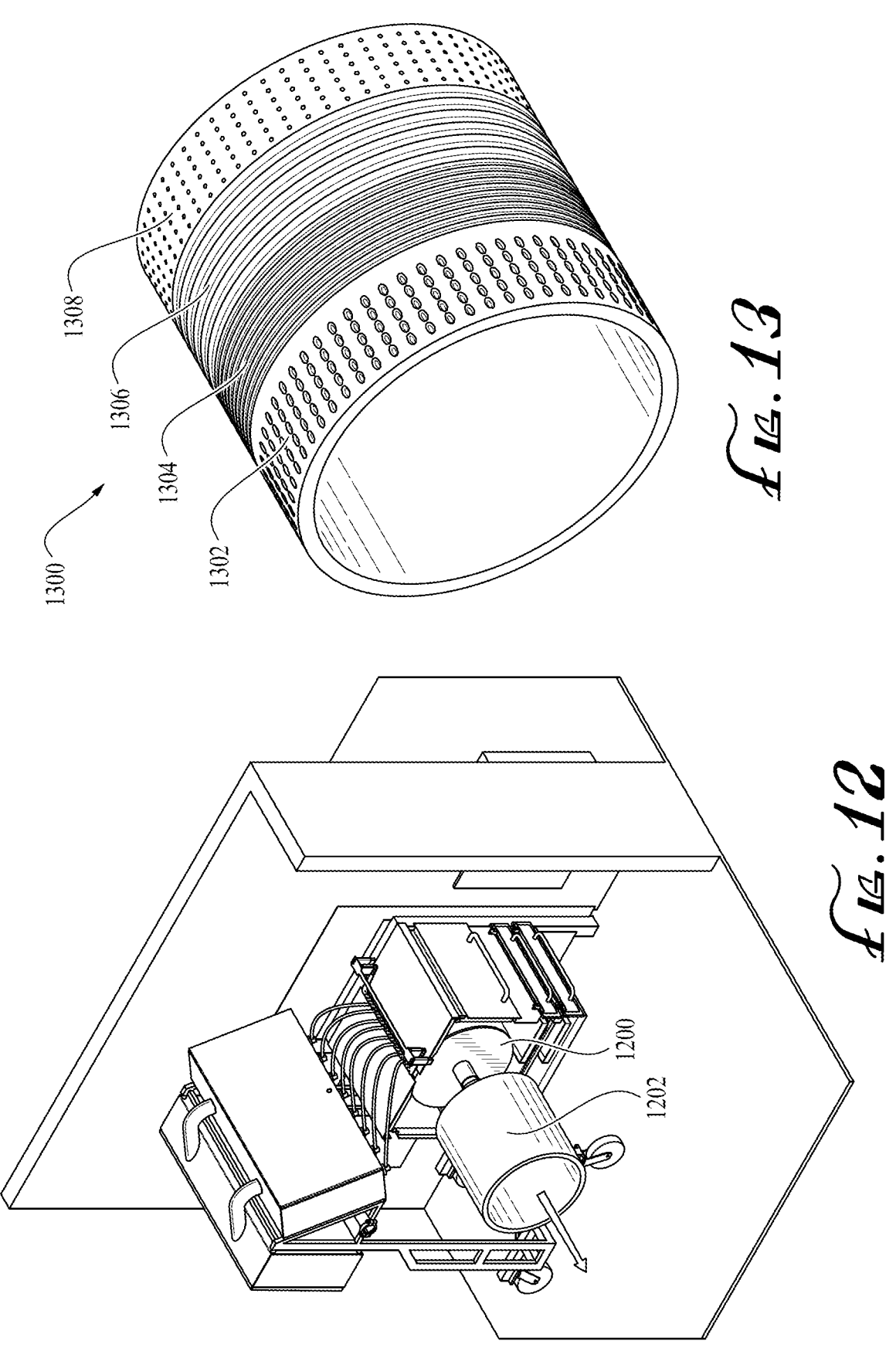
FIG. 12 illustrates the freezer system of FIG. 11 with components removed to illustrate a removable drum sleeve in accordance with one embodiment.
FIG. 13 illustrates an example embodiment of a removable drum sleeve for producing dosage units of different sizes, shapes, and configurations.

FIGS. 12-13 collectively illustrate a removable drum sleeve 1300 for use with the freezer system 1100. As noted previously, the geometric dimensions of the frozen dosage units 30 are controllable, at least in part, based on the corresponding geometric dimension of the cavities (e.g., cavities 106) on the outer surface 104 of the drum 102 (see FIG. 1). Accordingly, with reference to FIGS. 12 and 13, in some embodiments, the drum 1200 may be accessed by removing a portion of the drum frame. With reference to FIG. 12, one of the support structures of the drum frame has been removed. After removing the support structure to expose the drum 1200, the existing drum sleeve 1202 may be removed from the drum 1200 and replaced with another drum sleeve 1300 to create frozen dosage units 30 having any suitable geometric configuration. To establish a frame of reference, the drum sleeve 1300 is shown with four distinct pattern zones for creating different frozen dosage units 30 to provide a broad range of configurations. While a single drum sleeve 1300 may include multiple distinct patterns to produce frozen dosage units 30 of various shapes and sizes in one cycle, a streamlined manufacturing process will likely use a drum sleeve 1300 with one consistent pattern to avoid having to sort frozen dosage units 30 after production. With reference to FIG. 13, the drum sleeve 1300 may include any suitable pattern, such as: an oval pocket 1302 to create roughly oval-shaped frozen dosage unit 30, a narrow groove pattern 1304 and a wider groove pattern 1306 that may create circular or oval-shaped frozen dosage units 30 depending on the amount of liquid formulation dispensed, the rotational speed of the drum, and/or the freezing temperature of the outer surface of the drum, and a circular pocket 1308 to create round, pill-shaped frozen dosage units 30.

Figure 14:
FIG. 14 is a flow chart illustrating a method of making a solid dosage unit in accordance with one embodiment.
Figure 14:
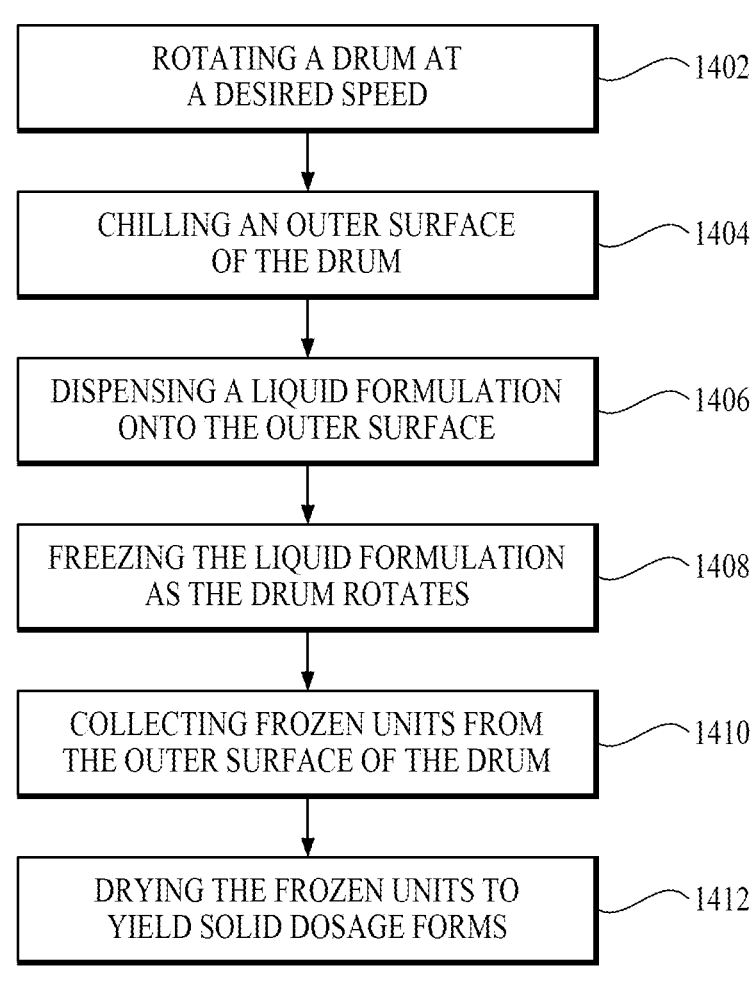

FIG. 14 is a flow chart illustrating a method 1400 for bulk manufacture of unit dosage forms in accordance with one embodiment. The method 1400 may comprise any number of steps employing any of the systems 100, 500, 1100 as described above, or at least one or more components of such a system. With reference to FIG. 14, method 1400 begins at step 1402 where the drum is rotated at a desired speed. As described previously, the drum has an outer surface comprising a plurality of cavities that may include any suitable configuration, such as pockets and grooves as described previously. At step 1404, the outer surface of the drum is chilled to a very low temperature using any suitable methodology. In some embodiments, the chilling step may include delivering a cryogen to the drum such that the cryogen comes into thermal contact with the outer surface of the drum as described previously. Preferably, the temperature of the outer surface of the drum ranges from between −50° C. to about −150° C., depending on various factors as further discussed below. At step 1406, a dispenser system dispenses a portion of a liquid formulation comprising a therapeutic agent into each of the one or more of the cavities on the outer surface of the drum. The liquid formulation is dispensed via the dispenser system while the drum rotates at the desired speed. At step 1408, the dispensed portion of the liquid formulation is frozen to a target level on the outer surface of the drum as the drum continues to rotate. In some embodiments, the dispensed portion is frozen to a solid state substantially throughout its entire volume.

In various embodiments, one or both of the outer surface temperature and the rotation speed of the drum may be selected to achieve freezing, at step 1408, of dispensed portions of the liquid formulation within a desired time frame and at a desired level of freezing. For example, step 1404 above may comprise chilling the outer surface to a temperature that will achieve very rapid or substantially instantaneous freezing of the dispensed portion of liquid formulation after contact with the outer surface of the drum. In other embodiments, the temperature of the outer surface of the drum may be selected to achieve freezing based upon the rotation cycle of the drum. For example, in some embodiments, the temperature may be selected such that the dosage unit is frozen in less than one rotation cycle of the drum. In other embodiments, the temperature may be selected to achieve freezing within one-quarter or one-half rotation of the drum. It will be understood, however, that the rotation speed of the drum may also be selected either in combination with or separately from the temperature of the outer surface of the drum to ensure the liquid formulation is sufficiently frozen as desired.

In other embodiments, the temperature of the outer surface described with reference to step 1404 may also be selected based in part upon the volume of each dispensed portion, which in turn may be selected in view of the amount of therapeutic agent to be delivered by the resulting dosage form. In some embodiments, the dispensed portion from the dispenser comprises an amount of liquid formulation selected to provide a specific dose of therapeutic agent. For example, the dispensed portion may have a volume of about 0.01 μl to about 1.0 ml. In such embodiments, the temperature of the outer surface of the drum may broadly range from between −50° C. to about −150° C. depending on the particular composition of the liquid formulation, the rotation speed of the drum, and/or other suitable factors.

Freezing time and other aspects of the freezing process described with reference to method 1400 may depend upon the physical and chemical characteristics of the liquid formulation as noted above. Accordingly, in some embodiments, method 1400 may further include the step of characterizing the liquid formulation to determine one or more of these characteristics, such as a phase transition temperature of the formulation, e.g., its glass transition temperature ($T_g$). In some embodiments, this step may comprise conducting thermogravimetric analysis (TGA), differential scanning calorimetry (DSC), freeze-drying microscopy (FDM), or a combination of these techniques. Thereafter, step 1404 may include selecting the chilling temperature of the outer surface based upon the characteristics of the liquid formulation.

Returning to FIG. 14, at step 1410, the frozen dosage units are collected from the cavities. As described previously, the frozen dosage units may simply fall from the rotating drum into a collection tray positioned underneath the drum, where the tray may be chilled to preserve the frozen units in a frozen state. For example, in one embodiment, a portion of liquid formulation may be dispensed, at step 1406, onto a location of the outer surface of the drum near the highest point of its orbital path, then permitted to freeze into a frozen unit, at step 1408. The frozen unit is subsequently removed from the outer surface of the drum near its lowest orbital point. In some embodiments, this process may comprise allowing the frozen unit to fall out of its cavity as noted above. As discussed previously, the morphology, chemistry, and temperature of the outer surface of the drum may be selected to result in little to no adherence between the frozen unit and the cavity to simplify the collection process.

In other embodiments, however, the method 1400 may further include the step of dislodging the frozen dosage units from the cavities, such as via a dislodging mechanism that enters each cavity while the drum rotates and contacts the frozen dosage units to remove them from the cavities. As mentioned previously, one aspect of the present disclosure is the ability to produce and package solid dosage forms in bulk without requiring a unit-dose packaging step. Accordingly, step 1410 may further include collecting multiple frozen units into a batch before subjecting them to further processing.

Finally, at step 1412, the collected frozen dosage units are dried to yield solid dosage forms. The drying process reduces the water content of the frozen dosage forms to provide stability for packaging and storage, while preserving their physical structure as well as the potency of therapeutic agent included therein. Drying may include various suitable processes, such as subjecting the frozen units to lyophilization or vacuum drying. In some embodiments, drying includes placing the collection tray containing a batch of frozen dosage units into a freeze dryer and subjecting them to a lyophilization process designed to produce solid dosage forms having desired characteristics. In some embodiments, the drying step is adapted to produce solid dosage forms having a selected water content, for example below about 3% w/w. In some embodiments, the drying step is adapted to produce solid dosage forms having a selected water activity level, for example from about 0.02 μl to about 300 μl. The lyophilized dosage forms may be packaged in bulk for storage and/or for shipping. The bulk quantity may also be apportioned and packaged in unit dosage formats, or into multiple packaging containers containing specific numbers of doses. In some embodiments, the batch of dosage forms may be processed for storage and/or shipping after being collected from the drum, i.e., without an intervening drying step. This approach may be used, for example, in cases where the dosage forms comprise a therapeutic agent that is intolerant of desiccation.

As noted previously, various parameters within the steps of method 1400 described above may be selected so as to produce solid dosage forms having desired characteristics. In various embodiments, the nature and quantity of the solid dosage forms may be determined at least in part by any of the following: the configuration of the outer surface of the drum; the temperature of the outer surface; the mode and speed of rotation of the drum; the properties of the liquid formulation, and the manner of dispensing the liquid formulation onto the drum. It should be noted however, that the foregoing is not intended to be exhaustive or limiting of the possible combinations of parameters that may be employed by one of skill in the relevant art with the aid of the present disclosure.

Accordingly, in some embodiments, method 1400 may further involve the step of selecting the configuration of the outer surface of the drum, including the surface morphology, surface chemistry, the form and arrangement of the cavities, the manner of dispensing the liquid formulation during rotation of the drum, or any combination of these. For example, the method may include dispensing a portion of liquid formulation into a groove on the outer surface while rotating the drum, such that each portion is dispensed near the uppermost position of the outer surface of the drum. However, it will also be appreciated that the liquid formulation may be delivered onto the drum at various positions. In some embodiments, the leading end of the dispensed portion of the liquid formulation is drawn out from the rest of the dispensed portion by the rotating drum, so that freezing of the portion results in an elongated frozen unit. The length of the frozen unit is determined by the dispensing duration relative to the rotation cycle length, while its width, height, and shape is determined at least in part by the width, depth, and cross-sectional shape of the cavities on the outer surface of the drum. As noted above, a plurality of such frozen units may be created within one rotation of the drum by dispensing multiple portions in each cavity, and further by utilizing multiple cavities, i.e., having a separate nozzle aligned with each cavity as described previously.

In another example embodiment, the drum may include an outer surface on which a plurality of discrete pockets is present, and the dispensing step 1406 of method 1400 may include dispensing the liquid formulation in a selected spatial and temporal pattern during rotation of the drum so as to place a portion of the formulation into each of a plurality of the pockets. The spatial and temporal pattern is selected so that a nozzle dispenses formulation at points in the rotation cycle when a cavity is adjacent the nozzle's orifice. In some embodiments, the method 1400 may further include slowing or interrupting the rotation of the drum at such points to allow a portion of the liquid formulation to be completely dispensed into each pocket.

As described, the methods and the related systems illustrated in the figures provide a streamlined process for manufacturing frozen dosage forms in bulk. It should be understood that in some embodiments, certain of the steps in method 1400 as described above may be combined, altered, varied, and/or omitted without departing from the principles of the disclosed subject matter. Further, it is intended that subject matter disclosed in one portion herein can be combined with the subject matter of one or more of other portions herein as long as such combinations are not mutually exclusive or inoperable. In addition, many variations, enhancements and modifications of the systems and methods described herein are possible.

The present disclosure further encompasses liquid formulations that are suited for use with the freezer systems 100, 500, 1100 described above and the related methods 1400 in making dried (e.g., lyophilized) solid dosage forms. In particular, the liquid formulations may be formed into dosage forms that are stable for packaging, storage, and handling in bulk and that retain a high level of therapeutic potency to be realized upon rehydration and/or administration. The liquid formulations are further useful for dosage forms that readily disintegrate in rehydrating conditions, such as in a solvent or upon administration by oral or transmucosal routes. Encompassed dosage forms include, without limitation, pastilles, tablets, powders, suppositories, and sachets. The liquid formulation may be adapted for effective dosing and delivery of a number of types of suitable therapeutic agents, including small molecules, botanical isolates, biotherapeutic molecules and macromolecules, nucleic acids, and cellular agents, such as stem cells and probiotics.

In some embodiments, a liquid formulation may comprise a mixture of a therapeutic agent and one or more excipients. Depending on the nature of the therapeutic agent and other ingredients, the liquid formulation may be prepared as a solution, a suspension, an emulsion, or a slurry. For example, a liquid formulation for making dosage form comprising a water-soluble small molecule may be prepared as an aqueous solution. To facilitate precise and consistent dosage among units and across the process, the liquid formulation may be prepared so that the therapeutic agent is homogeneously distributed within the formulation.

Excipients may include, without limitation, one or more of cryopreservatives, lyopreservatives, bulking agents, absorption enhancers, disintegrants, flavorings, sweeteners, surfactants, and thickeners. As used herein, "cryopreservatives" refers to compounds that, when added to a mixture comprising a therapeutic agent, accommodate freezing of the mixture without substantial loss of potency of the therapeutic agent upon rehydration or reconstitution. With particular respect to cell-based therapeutic agents, cryopreservatives can minimize or prevent intracellular ice crystal formation, osmotic imbalance and other freezing-related phenomena that reduce cell viability. Suitable cryopreservatives include, without limitation, mono-, di-, and polysaccharide sugars, such as sucrose or trehalose, dimethyl sulfoxide (DMSO), glycerol, propylene glycol and ethylene glycol. As used herein, "lyopreservatives" refers to compounds that, when added to a mixture comprising a therapeutic agent, allows lyophilization of the mixture without substantial loss of potency of the therapeutic agent upon rehydration or reconstitution. Suitable lyopreservatives include, without limitation, disaccharide sugars including sucrose, lactulose, lactose, maltose and trehalose; polyalcohols; raffinose and other non-reducing polysaccharides, and their derivatives.

Bulking agents may include various materials used for adding bulk and structure, particularly in solid dosage forms. In some embodiments, the bulking agent may comprise a carbohydrate base selected from the following group: mannitol, dextrose, sucrose, lactose, maltose, maltodextrin and lactose. Examples of other bulking agents include, without limitation, calcium hydrogen phosphate, microcrystalline cellulose, silicates, magnesium oxide, talc, potato or corn starch, isomalt, and polyvinyl alcohol. In particular, bulking agents may be selected to provide structural integrity when the dosage form is dry, and rapid disintegration in the presence of a liquid.

One or more absorption enhancers may be included to enhance penetration of the epithelium or other target membrane by the therapeutic agent, particularly in cases where the therapeutic agent comprises a large molecule or a highly hydrophilic molecule. Examples include quaternary ammonium salts, polyethylene glycol and polyethylene glycol esters, natural and synthetic surfactants, fatty acids, fatty alcohols, bile salts and bile acids, sugar esters and chelators. In some embodiments, the liquid formulation may comprise a compound selected to enhance short-term expansion of transcellular and/or paracellular pathways for active components that are otherwise too large for these pathways. Such compounds include alkyl saccharides in which a sugar is linked to an alkyl side chain by a glycosidic, amide, ester or other linkage. In some embodiments, the absorption enhancer includes an alkyl glycoside, particularly one comprising an alkyl having a carbon chain length of C6 to C18, or more particularly, C12 to C16 or C12 to C14. Suitable alkyl glycosides include, without limitation, dodecyl maltoside, tetradecyl maltoside, and N-lauryl-b-d-maltopyranoside.

The systems and methods described herein may be adapted in conjunction with the liquid formulation to create a solid matrix that readily disintegrates upon administration. In some embodiments, a disintegrant may be added. Suitable disintegrants include crosslinked polymers such as crosslinked polyvinyl pyrrolidone and crosslinked sodium carboxymethylcellulose.

Thickeners serve to maintain the therapeutic agent in homogenous suspension and thereby achieve uniform distribution throughout the mixture. The thickener also contributes to formation of the matrix and can provide a more palatable mouth feel before and during disintegration in oral dosage forms. In some embodiments, the thickener is a gum. Suitable gums include, without limitation, xanthan gum, carrageenan gums, galactomannan gums, acacia, guar, and tragacanth gum.

Surfactants may also be included to impart characteristics of potential benefit. For example, surfactants may be included for enhancing dispersion of the ingredients and preventing adhesion of a frozen unit to the cavity in which it is formed. Examples of pharmaceutically acceptable surfactants include: polyoxyethylene castor oil derivates, e.g. polyoxyethyleneglycerol triricinoleate or polyoxyl 35 castor oil, or polyoxyethyleneglycerol oxystearate such as polyethylenglycol 40 hydrogenated castor oil or polyethylenglycol 60 hydrogenated castor oil; or block copolymers of ethylene oxide and propylene oxide, also known as polyoxyethylene polyoxypropylene block copolymers or polyoxyethylene polypropyleneglycol; or a mono fatty acid ester of polyoxyethylene (20) sorbitan, e.g. polyoxyethylene (20) sorbitan monooleate, polyoxyethylene (20) sorbitan monostearate, polyoxyethylene (60) sorbitan monostearate, polyoxyethylene (20) sorbitan monopalmitate, or polyoxyethylene (20) sorbitan monolaurate.

Flavorings and sweeteners may be included in the liquid formulation to provide sensory appeal and mask bitterness of other ingredients. Flavorings may include any suitable natural, artificial, or combined natural and artificial flavoring or flavor enhancer, such as flavored oils, fruit preparations, maltol, ethyl maltol, citric acid, ascorbic acid or acetaldehyde. In other embodiments, fruit powders, concentrates, or purees may be used in higher amounts. In some embodiments, artificial sweeteners may be particularly useful because their potency permits using a minimal amount. Suitable sweeteners include acesulfame-K, aspartame, sodium saccharin, calcium saccharin, and mono-ammonium glycyrrihizinate (MAG).

Certain characteristics of the liquid formulation may have particular significance with respect its use in the systems and methods described above. For example, the viscosity of the formulation may affect the flow rate at which it can be dispensed via the nozzles, as well as its propensity to fill and conform to a cavity with a given shape. Each of these factors can be a consideration in the ability to control the amount of therapeutic agent in a dosage form having a given shape. In addition, the viscosity of the liquid formulation may impact the time it takes to freeze at a given temperature of the drum outer surface. With rapid freezing, the formation of large ice crystals can be avoided, which may be of particular benefit for dosage forms where the therapeutic agent comprises cells or biological macromolecules, which can be damaged by the crystal formation that occurs during slow freezing. In some embodiments, the liquid formulation can have a viscosity of about 0.1 cP to about 1000 cP, or from about 20 cP to about 150 cP.

The present disclosure also encompasses solid dosage forms made by employing systems, methods and materials described herein. In some embodiments, the solid dosage form comprises a pharmaceutically effective amount of a therapeutic agent, 0.1-3.0% of a gum, and 10-60% of a carbohydrate base. In certain embodiments, the solid dosage form may comprise (by dry weight): a therapeutic agent in the amount of 1-60% (preferably in the amount of 10-60%), a carbohydrate base in an amount of 10-60%, a gum in an amount of 0.1-3.0%, flavoring in an amount of 0.001-5.0%, a surfactant in an amount of less than 1%, and a sweetener in an amount less than about 1%.

The present disclosure may be better understood by reference to the following specific examples for liquid formulations and employed freeze tests.

EXAMPLES

An exemplary liquid formulation (Formulation 1) according to an embodiment contains the following ingredients:

| INGREDIENT | AMOUNT (% WET WT.) |
|---|---|
| ENCAPSULATED ACETAMINOPHEN (APAP) | 35.00 |
| MANNITOL | 30.00 |
| XANTHAN GUM | 0.30 |
| MONO-AMMONIUM GLYCYRRIHIZINATE (MAG) | 0.30 |
| ASPARTAME | 0.15 |
| WINTERGREEN FLAVOR | 1.00 |
| POLYSORBATE 60 | 0.01 |
| DISTILLED WATER | 33.24 |

In the above example, the encapsulated acetaminophen used was Durkote APAP 145-75 obtained from Van Den Bergh Food Ingredients Group of Lisle, Ill, the gum was Kelco Xanthan Gum K1B111, and the flavoring was DM Wintergreen 1348.

Further exemplary liquid formulations (2-81) according to embodiments of the present disclosure contain the ingredients shown below:

| | FORMULATION | | | |
|---|---|---|---|---|
| | 2 | 3 | 4 | 5 |
| | Flavor #1 | Flavor #2 | Flavor #3 | Flavor #2 |
| INGREDIENT (% w/w) | Control % | Control % | Control % | Reduced % |
| ENCAPSULATED ACETAMINOPHEN | 35.00 | 35.00 | 42.00 | 42.00 |
| MANNITOL | 30.00 | 30.00 | 22.00 | 22.00 |
| MALTRIN | — | — | 2.00 | 2.00 |
| XANTHAN GUM | 0.30 | 0.30 | 0.30 | 0.30 |
| MAG | 0.30 | 0.30 | 0.30 | 0.30 |
| ASPARTAME | 0.15 | 0.15 | 0.15 | 0.15 |
| FLAVOR #1 | 1.20 | — | 1.20 | — |
| FLAVOR #2 | — | 1.20 | — | 1.20 |
| POLYSORBATE 60 | 0.01 | 0.01 | 0.01 | 0.01 |
| DISTILLED WATER | 33.04 | 33.04 | 32.04 | 32.04 |
| TOTAL | 100.00 | 100.00 | 100.00 | 100.00 |
| g wet mix/ 325 mg tablet | 1.20 | 1.20 | 1.00 | 1.00 |

| | Formulations 6-19 | | | | | | | | | | | | | |
|---|---|---|---|---|---|---|---|---|---|---|---|---|---|---|
| Ingredient (gm) | 6 | 7 | 8 | 9 | 10 | 11 | 12 | 13 | 14 | 15 | 16 | 17 | 18 | 19 |
| ACETAMINOPHEN | 5.00 | 5.00 | 5.00 | 5.00 | 5.00 | 5 | 5 | 5 | 0.25 | 2.5 | 2.5 | 2.5 | 2.5 | 2.5 |
| DEXTROSE | 9.00 | 9.00 | — | 9.00 | — | 8 | 8 | 5.8 | — | 4.3 | 4.3 | 5 | 5 | 4.5 |
| SUGAR | — | — | 9.00 | — | 9.00 | 2 | 2 | 3 | 0.32 | — | — | 2 | 2 | 1.35 |
| XANTHAN GUM | 0.10 | 0.10 | 0.10 | 0.10 | 0.10 | 0.02 | 0.03 | 0.03 | 0.05 | 0.02 | 0.03 | 0.03 | 0.03 | 0.03 |
| POLYSORBATE | 0.02 | 0.02 | 0.02 | — | — | — | 0.02 | 0.05 | 0.05 | 0.02 | 0.02 | 0.02 | — | 0.02 |
| MAG | 0.10 | 0.10 | 0.10 | — | .13 (110) | 0.1 | — | 0.1 | 0.03 | 0.09 | 0.1 | 0.1 | 0.15 | 0.1 |
| ACESULFAME K | 0.02 | 0.03 | 0.03 | — | — | — | 0.05 | 0.05 | — | — | — | — | — | — |

-continued

| Formulations 6-19 | | | | | | | | | | | | | | |
| Ingredient (gm) | 6 | 7 | 8 | 9 | 10 | 11 | 12 | 13 | 14 | 15 | 16 | 17 | 18 | 19 |
|---|---|---|---|---|---|---|---|---|---|---|---|---|---|---|
| SACCHARIN | — | — | — | 0.90 | 0.54 | — | — | — | — | — | — | — | — | — |
| FLAVOR #1 | — | — | — | 0.30 | — | 0.4 | 0.7 | 0.5 | 0.1 | 0.1 | — | 0.12 | — | — |
| FLAVOR #2 | — | 0.01 | 0.02 | — | — | — | — | — | — | — | — | — | — | — |
| WATER | 35.00 | 16.00 | 16.00 | 14.00 | 14 | 14 | —15.5 | 1.5 | 1.5 | 15 | 10 | 8.35 | 6.3 | 4.5 |
| TOTAL | 49.24 | 30.26 | 30.25 | 28.40 | 28.77 | 29.52 | 29.8 | 31 | | 22.03 | 16.95 | 18.12 | 15.98 | 13 |
| WET ING. | 35.00 | 16.00 | 16.00 | 14.30 | 14.23 | 14.4 | 14.7 | 16 | | 15.1 | 10 | 8.47 | 6.3 | 4.5 |
| DRY ING. | 14.24 | 14.26 | 14.25 | 34.10 | 14.54 | 15.12 | 15.1 | 14 | | 6.93 | 6.95 | 9.65 | 9.68 | 8.5 |
| # TABS | 18 | 18 | 18 | 17 | 17 | 16 | 17 | 17 | | — | | — | — | — |
| WT./TAB | 2.48 | 1.39 | 1.43 | 1.40 | 1.41 | 1.36 | 1.5 | 1.34 | | — | | 1.65 | 1.3 | 1.35 |
| MG APAP | 252 | 230 | 235 | 246 | 245 | 230 | 251 | 216 | | 170 | | 229 | 203 | 2.59 |

| Formulations 20-30 | | | | | | | | | | | |
| INGREDIENT (gm) | 20 | 21 | 22 | 23 | 24 | 25 | 26 | 27 | 28 | 29 | 30 |
|---|---|---|---|---|---|---|---|---|---|---|---|
| ACETAMINOPHEN | 5.00 | 5 | 5 | 5 | 5 | 5 | 5 | 5 | 5 | 50 | 5 |
| DEXTROSE | 9.00 | 8.6 | 9 | 9 | 10 | 8 | 8 | 9 | 10 | 100 | 10 |
| XANTHAN GUM | 0.10 | 0.06 | 0.08 | 0.1 | 0.1 | 0.8 | 0.8 | 0.8 | 0.1 | 1 | 0.1 |
| POLYSORBATE | 0.02 | 0.04 | 0.02 | 0.02 | 0.02 | 0.02 | 0.02 | 0.02 | 0.04 | 0.4 | 0.02 |
| MAG | 0.10 | 0.2 | 0.15 | 0.15 | 0.15 | 0.2 | 0.2 | 0.3 | 0.5 | 5 | 0.2 |
| ACESULFAME K | 0.03 | — | — | — | — | — | 0.04 | 0.04 | — | | 0.01 |
| SACCHARIN | — | — | 1.5 | 2.5 | 2 | 1 | — | — | 1 | 10 | |
| FLAVOR #1 | 0.01 | — | — | — | — | — | — | — | | | |
| FLAVOR #2 | — | — | 0.1 | 0.15 | 0.15 | 0.12 | — | — | 0.2 | 0.32 | 0.15 |
| FLAVOR #3 | — | — | — | — | — | — | — | 0.3 | 0.35 | | |
| WATER | 16.00 | 20 | 16.00 | 15.00 | 12 | 14 | 14 | 20 | 15 | 150 | 12 |
| TOTAL | 30.26 | 33.9 | 31.85 | 31.92 | 29.42 | 28.42 | 27.64 | 34.79 | 31.84 | 316.72 | |
| WET ING. | 16.00 | 20 | 17.50 | 17.50 | 14.00 | 15 | 14 | 20 | 16 | 160 | |
| DRY ING. | 14.26 | 13.9 | 14.35 | 14.42 | 15.42 | 13.42 | 13.64 | 14.79 | 15.84 | 156.72 | |
| # TABS | 18 | | 18 | | 16 | 16 | 13 | | | 30 | |
| WT./TAB | 1.39 | | 1.42 | | 1.39 | 1.47 | 1.66 | | | 1.95 | |
| MG APAP | 230 | | 223 | | 236 | 259 | 300 | | | 308 | |

Formulations 31-38
ENCAPSULATED ACETAMINOPHEN (75% APAP: 6.67 G =
5 G APAP AND 1.67 G COTTONSEED OIL)

| INGREDIENT (gm) | 31 | 32 | 33 | 34 | 35 | 36 | 37 | 38 |
|---|---|---|---|---|---|---|---|---|
| ENCAPSULATED APAP | 6.67 | 6.67 | 6.67 | 6.67 | 6.67 | 6.67 | 6.67 | 6.67 |
| DEXTROSE | 9.00 | 8.6 | 9.00 | 9.00 | 9.00 | 8.6 | 8.6 | 8.6 |
| XANTHAN GUM | 0.10 | 0.06 | 0.10 | 0.10 | 0.10 | 0.06 | 0.06 | 0.06 |
| POLYSORBATE | 0.02 | 0.04 | 0.02 | 0.02 | 0.02 | 0.04 | 0.04 | 0.04 |
| MAG | 0.1 | 0.2 | 0.1 | 0.1 | 0.1 | 0.2 | 0.2 | 0.2 |
| ACESULFAME K | 0.05 | — | 0.03 | 0.03 | 0.03 | — | — | — |
| FLAVOR #1 | 0.01 | — | — | — | — | — | — | — |
| FLAVOR #2 | — | — | 0.15 | 0.15 | 0.15 | 0.15 | 0.15 | 0.15 |
| WATER | 16.00 | 20 | 18.00 | 20.00 | 22.00 | 19 | 18 | 17 |
| TOTAL | 30.26 | 35.57 | 34.07 | 36.07 | 38.07 | 34.72 | 33.72 | 32.72 |
| WET ING. | 16.00 | 20 | 18.00 | 20.00 | 22.00 | 19.00 | 18.00 | 18.00 |
| DRY ING. | 14.26 | 15.57 | 16.07 | 16.07 | 16.07 | 15.72 | 15.72 | 14.72 |
| # TABS | 18 | | | | | | | |
| WT./TAB | 1.39 | | | | | | | |
| MG APAP | 230 | | | | | | | |
| RESULTS | BEST | BEST | | | | | | |

Formulations 39-48
Varying Carbohydrate, Flavoring and Sweeteners

| INGREDIENT (gm) | 39 | 40 | 41 | 42 | 43 | 44 | 45 | 46 | 47 | 48 |
|---|---|---|---|---|---|---|---|---|---|---|
| REGULAR APAP OR | 12.5 | — | 12.5 | — | | | | | | |
| ENCAPSULATED APAP | — | 16.68 | — | 3.33 | 3.33 | 3.33 | 3.33 | 16.68 | 16.68 | 16.68 |
| DEXTROSE | 22.50 | 22.5 | 21.5 | | | | 3.67 | | 22.5 | |
| LACTOSE | | | | 3.67 | | | | | | |
| M100 | | | | | | 3.67 | | 15 | | 15 |
| MALTOSE | | | | | 3.67 | | | | | |
| XANTHAN GUM | 0.25 | 0.25 | 0.15 | 0.04 | 0.04 | 0.04 | 0.04 | 0.25 | 0.25 | 0.25 |
| POLYSORBATE | 0.05 | 0.05 | 0.1 | 0.01 | 0.01 | 0.01 | 0.01 | 0.05 | 0.05 | 0.05 |
| MAG | 0.25 | 0.25 | 0.5 | 0.05 | 0.05 | 0.05 | 0.05 | 0.25 | 0.25 | 0.25 |
| SACCHARIN | 2.5 | 2.5 | — | 0.5 | 0.5 | 0.5 | 0.5 | 2.5 | 2.5 | 2.5 |
| FLAVOR | 0.50 | 0.5 | 0.375 | 0.08 | 0.08 | 0.08 | 0.08 | | 0.5 | 0.5 |
| RASPBERRY PUREE | | | | | | | | 10 | | 10 |
| ACETALDEHYDE | | | | | | | | | 0.08 | 0.08 |
| WATER | 40.00 | 40 | 50 | 9 | 9 | 9 | 9 | 35 | 40 | 35 |

Formulations 49-59

| INGREDIENT (gm) | 49 | 50 | 51 | 52 | 53 | 54 | 55 | 56 | 57 | 58 | 59 |
|---|---|---|---|---|---|---|---|---|---|---|---|
| (ACTUAL APAP) | 12.33 | 15.121% | 12.51 | 19.230 | 22.5 | 26.25 | 15.15 | 30.00 | 29.05 | 29.996 | 22.500 |
| ENCAPSULATED APAP | 16.68 | 20.162% | 16.68 | 25.642 | 30.000 | 35.00 | 20.20 | — | 35.00 | 36.140 | 30.000 |
| DEXTROSE | 22.50 | 27.197% | 22.50 | 24.848 | 20.000 | 20.00 | 27.20 | 20.00 | 20.00 | 20.000 | — |
| MANNITOL | — | — | — | — | — | — | — | — | — | — | 20.000 |
| XANTHAN GUM | 0.25 | 0.302% | 0.25 | 0.311 | 0.300 | 0.30 | 0.30 | 0.30 | 0.30 | 0.300 | 0.300 |
| POLYSORBATE | 0.05 | 0.060% | 0.05 | 0.062 | 0.000 | | 0.06 | 0.10 | 0.10 | 0.100 | 0.000 |
| MAG | 0.25 | 0.302% | 0.25 | 0.311 | 0.300 | 8.30 | 0.30 | 0.30 | 0.30 | 0.500 | 0.300 |
| SACCHARIN | 2.5 | 3.022% | 2.5 | | | | | | | | |
| ASPARTAME | — | — | — | 0.124 | 0.15 | 0.15 | | 0.15 | 0.15 | 0.200 | 0.150 |
| MALTOL | — | — | — | — | — | — | 0.25 | 1.00 | 0.50 | 0.200 | — |
| FLAVOR #1 | 0.50 | 0.604% | — | 0.621 | | | 0.60 | | | | |
| FLAVOR #2 | — | — | 0.025 | | 0.03 | 0.03 | | 0.05 | 0.05 | 0.060 | 0.030 |
| WATER | 40.00 | 48.350% | 40.00 | 48.081 | 49.220 | 44.22 | 51.09 | 48.00 | 43.60 | 44.000 | 49.220 |
| | | | | | | | | | | | |
| TOTAL | 82.73 | 100.000% | 82.255 | 100.00 | 100.00 | 100.00 | 100.00 | 99.90 | 100.00 | 101.50 | 100.00 |
| WET ING. | 42.50 | | 42.50 | | 49.22 | 44.22 | 51.09 | 48.00 | 43.60 | | |
| DRY ING. | 40.23 | | 39.755 | | 50.78 | 55.76 | 48.91 | 51.93 | 56.40 | | |
| 250 mg wet wt. | 1.65 | | 1.65 | 1.3 | 1.10 | 0.94 | 1.63 | 0.83 | 0.86 | 0.83 | 1.10 |
| 250 mg wet wt. | 0.80 | | 0.80 | | | | | | | | |
| 500 mg wet wt. | 3.30 | | 3.30 | 2.6 | 2.2 | 1.88 | | 1.66 | 1.72 | 1.66 | 2.20 |

Formulation 60

| INGREDIENT | % | G/250 mg | G/325 mg | g/500 mg |
|---|---|---|---|---|
| DEXTROSE | 27.195% | 0.449 | 0.584 | 0.897 |
| ENCAPSULATED APAP | 20.161% | 0.333 | 0.433 | 0.665 |
| FLAVOR #1 | 0.604% | 0.101 | 0.013 | 0.020 |
| XANTHAN GUM | 0.302% | 0.005 | 0.006 | 0.010 |
| MAG | 0.302% | 0.005 | 0.006 | 0.010 |
| CALCIUM SACCHARIN | 0.066% | 0.001 | 0.001 | 0.002 |
| POLYSORBATE | 0.060% | 0.001 | 0.001 | 0.002 |
| WATER | 51.305% | 0.847 | 1.102 | 1.693 |
| TOTAL | 100.000% | 1.650 | 2.148 | 3.300 |

Formulation 61

| INGREDIENT | % | G/250 mg | G/325 mg | g/500 mg |
|---|---|---|---|---|
| ENCAPSULATED APAP | 35.000 | 0.333 | 0.434 | 0.665 |
| STALEYDEX | 20.000 | 0.190 | 0.248 | 0.380 |
| XANTHAN | 0.300 | 0.003 | 0.004 | 0.006 |
| MAGNASWEET | 0.300 | 0.003 | 0.004 | 0.006 |
| ASPARTAME | 0.150 | 0.001 | 0.002 | 0.003 |
| FLAVOR | 0.600 | 0.006 | 0.007 | 0.011 |
| WATER | 43.650 | 0.415 | 0.541 | 0.829 |
| TOTAL | 100.000 | 0.950 | 1.240 | 1.900 |

23

Formulations 62-65

| INGREDIENT (%) | % | .5 ZEIN 62 | .7 ZEIN 63 | 1.0 ZEIN 64 | 1.0 ZEIN 65 |
|---|---|---|---|---|---|
| ACTUAL APAP | 26.25 | 26.25 | 26.25 | 26.25 | 26.25 |
| ENCAPSULATED APAP | 35.00 | 27.63 | 28.23 | 29.17 | 29.17 |
| MANNITOL | 20.00 | 20.00 | 20.00 | 20.00 | 25.00 |
| XANTHAN GUM | 0.30 | 0.30 | 0.30 | 0.30 | 0.30 |
| CORN OIL | — | 0.50 | 0.50 | 0.50 | 0.50 |
| MAG | 0.30 | 0.30 | 0.30 | 0.30 | 0.30 |
| ASPARTAME | 0.15 | 0.15 | 0.15 | 0.15 | 0.15 |
| FLAVOR | 0.60 | 0.60 | 0.60 | 0.60 | 0.60 |
| WATER | 43.65 | 50.52 | 49.92 | 48.98 | 43.98 |
| TOTAL | 100.00 | 100.00 | 100.00 | 100.00 | 100.00 |
| g/250 mg tablet | | 0.95 | 0.95 | | |
| g/325 mg tablet | | 1.24 | 1.24 | | |
| g/500 mg tablet | | 1.91 | 1.90 | | |

Acetaminophen encapsulated in zein (corn protein soluble in alcohol)

Formulations 66-69

| INGREDIENT (%) | 66 | 67 | 68 | 69 |
|---|---|---|---|---|
| ACTUAL APAP | 27.09 | 27.09 | 27.09 | 27.09 |
| ENCAPSULATED APAP | 35.00 | 35.00 | 35.00 | 35.00 |
| DEXTROSE | 20.00 | — | | |
| MANNITOL | — | 20.00 | 25.00 | 25.00 |
| XANTHAN GUM | 0.30 | 0.30 | 0.30 | 0.30 |
| MAG | 0.30 | 0.30 | 0.30 | 0.30 |
| ASPARTAME | 0.15 | 0.15 | 0.20 | 0.15 |
| FLAVOR | 0.60 | 0.60 | 0.75 | 0.60 |
| WATER | 43.65 | 43.65 | 38.45 | 38.65 |
| TOTAL | 100.00 | 100.00 | 100.00 | 100.00 |

24

-continued

Formulations 66-69

| INGREDIENT (%) | 66 | 67 | 68 | 69 |
|---|---|---|---|---|
| g/250 mg tablet | 0.92 | 0.92 | | |
| g/325 mg tablet | 1.20 | 1.20 | | |
| g/500 mg tablet | 1.85 | 1.85 | | |

Formulation 70-75

| INGREDIENT (% w/w) | 70 | 71 | 72 | 73 | 74 | 75 |
|---|---|---|---|---|---|---|
| ACTUAL APAP | 27.09 | 27.09 | 27.09 | 27.09 | 27.09 | 27.09 |
| ENCAPSULATED APAP | 35.00 | 35.00 | 35.00 | 35.00 | 35.00 | 35.00 |
| MANNITOL | 30.00 | 15.00 | 20.00 | 25.00 | 20.00 | 20.00 |
| MALTRIN | — | 15.00 | 10.00 | 10.00 | 5.00 | — |
| XANTHAN GUM | 0.30 | 0.30 | 0.30 | 0.30 | 0.30 | 0.30 |
| MAG | 0.30 | 0.30 | 0.30 | 0.30 | 0.30 | 0.30 |
| ASPARTAME | 0.15 | 0.15 | 0.15 | 0.15 | 0.15 | 0.15 |
| FLAVOR | 0.90 | 0.90 | 0.90 | 0.90 | 0.90 | 0.90 |
| POLYSORBATE | 0.01 | 0.01 | 0.01 | 0:01 | 0.01 | 0.01 |
| WATER | 33.34 | 33.34 | 33.34 | 33.34 | 33.34 | 33.34 |
| TOTAL | 100.00 | 100.00 | 100.00 | 100.00 | 100.00 | 100.00 |
| g/250 mg tablet | 0.92 | 0.92 | 0.92 | 0.92 | 0.92 | |
| g/325 mg tablet | 1.20 | 1.20 | 1.20 | 1.20 | 1.20 | |
| g/500 mg tablet | 1.83 | 1.85 | 1.85 | 1.85 | 1.85 | |
| approx dry wts | | | | | | |
| g/325 mg tablet | 0.80 | 0.80 | 0.80 | 0.80 | 0.74 | 0.80 |
| g/500 mg tablet | 1.23 | 1.23 | 1.23 | 1.23 | 1.23 | |

Formulations 76-81

| INGREDIENT (% w/w) | 76 | 77 | 78 | 79 | 80 | 81 |
|---|---|---|---|---|---|---|
| ACTUAL APAP | 27.09 | | 27.09 | 27.00 | 27.23 | 27.09 |
| ENCAPSULATED APAP | 35.00 | 70.00 | 35.00 | — | 25.50 | 35.00 |
| MANNITOL | 30.00 | 60.00 | 30.00 | 30.00 | 30.00 | 30.00 |
| XANTHAN GUM | 0.30 | 0.60 | 0.30 | 0.30 | 0.30 | 0.30 |
| CARRAGEENAN | | | | | | 0.30 |
| MAG | 0.30 | 0.60 | 0.30 | 0.30 | 0.30 | 0.30 |
| ASPARTAME | 0.15 | 0.30 | 0.15 | 0.15 | 0.15 | 0.15 |
| FLAVOR | 1.00 | 2.00 | 0.90 | 0.90 | 0.90 | 0.90 |
| ASCORBIC ACID | — | | 0.10 | — | — | 0.30 |
| POLYSORBATE | 0.01 | 0.02 | 0.01 | 0.01 | 0.01 | 0.01 |
| WATER | 33.24 | 66.48 | 33.24 | 41.34 | 40.84 | 33.04 |
| TOTAL | 100.00 | 200.00 | 100.00 | 100.00 | 100.00 | 100.00 |
| g/325 mg tablet | 1.20 | | 1.20 | 1.20 | 1.19 | |
| g/500 mg tablet | 1.85 | | 1.85 | 1.85 | 1.84 | |

Two exemplary formulations ("Sample A" and "Sample B") for providing enhanced intranasal delivery of insulin are described below:

| | Collagen Slurry (g) | Intravail A5 ™ (g) | 0.1M Sodium Phosphate (g) | Total Weight (g) | Collagen Solids (g) in Slurry | Collagen % Solids in Sample | Total % Solids in Sample |
|---|---|---|---|---|---|---|---|
| Sample A | 29.92 | 1.466 | 20 | 51.386 | 0.3614 | 0.703 | 3.556 |
| Sample B | 13.43 | 1.331 | 13.4 | 28.161 | 0.1622 | 0.576 | 5.302 |

Solid dosage forms were made using these formulations using various freezing and lyophilization regimes, the results of which are summarized below:

Freeze Tests:

| Sample Label | Freeze Method | Freeze Structure Results |
|---|---|---|
| A1 | Lab Freezer, −40 C. | Moderate intrusions in 6 of 7 cells |
| A2 | Blast Freezer, −25 F. | Rough surface layer, 1 intrusion in 14 cells |
| A3 | Dryer Freeze Cycle | Tight structure w/moderate intrusions in 7 of 7 cells |
| A4 | Freeze Plate | Tightest structure w/minor & moderate intrusions in all 23 cells |
| B1 | Lab Freezer, −40 C. | Major intrusions in 6 of 6 cells |
| B2 | Blast Freezer, −25 F. | Moderate "spill out" intrusions in 7 of 7 cells |
| B3 | Dryer Freeze Cycle | Tight structure w/moderate intrusions in 6 of 6 cells |
| B4 | Freeze Plate | Tightest structure w/minor & moderate intrusions in all 8 cells |

Lyo Cycle: Batch# E6073 Total DT = 26 hrs.

| Region | Time (hrs) | Temp (deg. C.) | Vacuum (microns) |
|---|---|---|---|
| 1 | 1 | −30 | <100 |
| 2 | 6 | Ramp −30 to 10 | <100 |
| 3 | 4 | Ramp 10 to 30 | <100 |
| 4 | 15 | 30 | <100 |

Dry Tests:

| Sample Label | % Moisture: Computrac 110C | Weight: Grams/ tablet | Release characteristics | Dry Structure |
|---|---|---|---|---|
| A1 | 0.763 | 0.034 | Easy | Good |
| A2 | 0.200 | 0.034 | Easy | Good |
| A3 | 0.866 | 0.036 | More difficult | OK |
| A4 | 0.187 | 0.035 | Easy | Good |
| B1 | 0.000 | 0.049 | Easy | Good |
| B2 | 0.000 | 0.045 | Easy | Good |
| B3 | 1.360 | 0.052 | More difficult, sticky | Breaks apart |
| B4 | 0.000 | 0.044 | Easy | Good |

The terms and descriptions used above are set forth by way of illustration only and are not meant as limitations in describing the disclosed systems and related methods. Those skilled in the art will recognize that many variations can be made to the details of the above-described embodiments without departing from the underlying principles of the invention

What is claimed is:

1. A method for bulk manufacture of unit dosage forms, the method comprising:

rotating a drum around a rotational axis at a rotational speed, the drum having an outer surface with a plurality of cavities formed thereon:

chilling the outer surface of the drum to a target temperature:

dispensing a liquid formulation comprising a therapeutic or biotherapeutic agent into one or more of the plurality of cavities while rotating the drum about its rotational axis;

freezing the liquid formulation within the one or more of the plurality of cavities to form a frozen unit in each of the one or more of the plurality of cavities;

collecting the frozen units from the one or more of the plurality of cavities; and drying the collected frozen units to form the unit dosage forms.

2. The method of claim 1, further comprising the step of selecting the target temperature for chilling the outer surface of the drum based on a rotational cycle of the drum, wherein the step of freezing the liquid formulation occurs within one rotational cycle of the drum after liquid formulation is dispensed.

3. The method of claim 1, wherein the target temperature of the outer surface of the drum ranges from between about −50° C. to about −150° C.

4. The method of claim 1, wherein chilling the outer surface of the drum further comprises delivering a cryogen into thermal contact with the outer surface.

5. The method of claim 4, wherein delivering the cryogen comprises injecting cryogen into an interior cavity of the drum.

6. The method of claim 1, wherein the liquid formulation has a temperature of about 4° C. to about 25° C. during dispensing.

7. The method of claim 1, wherein the drying step further comprises drying the collected frozen units to a water activity level ranging from about 0.02 to about 0.1.

8. The method of claim 1, wherein prior to dispensing the liquid formulation, the method further comprises characterizing the liquid formulation to determine a phase transition temperature of the liquid formulation, and wherein the target temperature of the outer surface of the drum is based on the phase transition temperature of the liquid formulation.

9. The method of claim 8, wherein characterizing the liquid formulation comprises conducting thermogravimetric analysis (TGA), differential scanning calorimetry (DSC), and/or freeze-drying microscopy (FDM).

10. The method of claim 1, further comprising adjusting the rotational speed of the drum during the step of dispensing the liquid formulation.

11. The method of claim 1, wherein the one or more of the plurality of cavities comprises discrete pockets.

12. The method of claim 1, wherein the outer surface comprises a removable drum sleeve and the plurality of cavities is formed thereon.

13. The method of claim 1, wherein at the target temperature, the liquid formulation is frozen within a one-half rotation of the drum.

14. The method of claim 1, wherein at the target temperature, the liquid formulation is frozen within a one-quarter rotation of the drum.

15. The method of claim 1, wherein the dispensed liquid formulation has a volume from about 0.01 μl to about 1.0 ml.

16. The method of claim 1, wherein during the collecting step, the frozen units fall into a collection tray positioned underneath the drum.

17. The method of claim 16, wherein the collection tray is chilled to a selected temperature to maintain the frozen units in a frozen state.

18. The method of claim 1, further comprising dislodging the frozen units from their respective cavities of the rotating drum prior to the collecting step.

19. The method of claim 1, wherein the drying step further comprises drying the collected frozen units to a water content below about 3% w/w.

20. The method of claim 1, wherein the outer surface is hydrophobic.

21. The method of claim 1, wherein the outer surface is configured to result in no adherence between the frozen unit in each of the one or more of the plurality of cavities.

* * * * *